(12) United States Patent
Dollings et al.

(10) Patent No.: US 6,683,107 B2
(45) Date of Patent: Jan. 27, 2004

(54) FURANS, BENZOFURANS, AND THIOPHENES USEFUL IN THE TREATMENT OF INSULIN RESISTANCE AND HYPERGLYCEMIA

(75) Inventors: Paul J. Dollings, Newtown, PA (US); Robert E. McDevitt, Somerset, NJ (US); Folake O. Adebayo, Cranbury, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/215,311

(22) Filed: Aug. 8, 2002

(65) Prior Publication Data

US 2003/0073709 A1 Apr. 17, 2003

Related U.S. Application Data

(62) Division of application No. 09/887,672, filed on Apr. 23, 2001, now Pat. No. 6,451,845, which is a continuation of application No. 09/564,469, filed on May 4, 2000, now Pat. No. 6,248,764, which is a division of application No. 09/307,691, filed on May 10, 2000, now Pat. No. 6,103,708.
(60) Provisional application No. 60/126,416, filed on May 12, 1998.

(51) Int. Cl.$^7$ .................... A61K 31/381; A61K 31/341; C07D 333/02; C07D 323/02
(52) U.S. Cl. ................ 514/438; 514/461; 514/465; 549/29; 549/429
(58) Field of Search .......................... 514/438, 336, 514/449, 361, 363, 365, 403, 406, 156, 461, 465, 448; 549/29, 429

(56) References Cited

U.S. PATENT DOCUMENTS

| | | | | |
|---|---|---|---|---|
| 4,117,151 A | * | 9/1978 | Descamps et al. | 514/469 |
| 5,596,106 A | | 1/1997 | Cullinan et al. | |
| 6,248,764 B1 | * | 6/2001 | Dollings et al. | 514/363 |
| 6,451,845 B1 | * | 9/2002 | Dollings et al. | 514/444 |

FOREIGN PATENT DOCUMENTS

| | | |
|---|---|---|
| DE | 31 10 460 | 12/1982 |
| DE | 33 42 624 | 3/1984 |

OTHER PUBLICATIONS

Theodor Eckert et al., Arch. Pharm., 1982, 569–570, 315(82).
Charles Goldenberg et al., Eur. J. Med. Chem., Chim. Ther., Jan–Feb 1977, 81–86, 12(1).
Kennan Fahey et al., Caplus DN 125:14122, WO 96/02248 Abstract.

* cited by examiner

Primary Examiner—Rita Desai
(74) Attorney, Agent, or Firm—Michael R. Nagy

(57) ABSTRACT

This invention provides compounds of Formula I having the structure

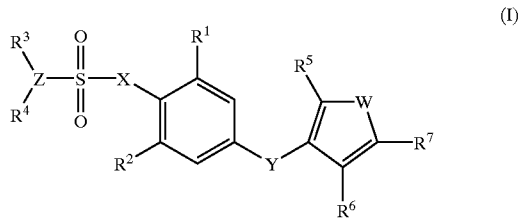

(I)

wherein $R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl substituted with trifluoromethyl, chloro, methoxy, or trifluoromethoxy;

$R^3$ and $R^4$ are each, independently, hydrogen, carboxyl, hydroxyl, hydoxyalkyl of 1–6 carbon atoms, alkoxy of 1–6 carbon atoms, perfluoroalkoxy of 1–6 carbon atoms, alkanoyloxy of 2–7 carbon atoms, perfluoroalkanoyloxy of 2–7 carbon atoms, arylalkoxy of 7–15 carbon atoms, aryloxy of 6–12 carbon atoms, aroyloxy of 6–12 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, alkylamino of 1–6 carbon atoms, dialkylamnino of 1–6 carbon atoms per alkyl group, tetrazolyl, mercapto, nitrile, nitro, amino, —NHSO$_2$CF$_3$, carbamoyl, carboxyaldehyde, halogen, acylamino, 3-hydroxy-cyclobut-3-ene-4-yl-1,2-dione, pyridyl, isoxazolyl, pyrimidyl or pyrimidyl substituted with mercapto, or tetronic acid;

$R^5$ is hydrogen, alkyl of 1–6 carbon atoms, perfluoroalkyl of 1–6 carbon atoms, naphthalenylmethyl, benzyl or benzyl substituted with halogen, $R^6$ and $R^7$ are each, independently, hydrogen, alkyl of 1–6 carbon atoms, or perfluoroalkyl of 1–6 carbon atoms, or $R^6$ and $R^7$ may be taken together as a diene unit having the structure —CH=CH—CH=CH—;

W is S or O,

X is —NR$^8$CH$_2$—, —NR$^8$—, or O;

$R^8$ is hydrogen or alkyl;

Y is carbonyl, methylene, ethyl, or —NHCH$_2$—;

Z is phenyl, pyridyl, naphthyl, thienyl, furyl, pyrrolyl, pyrazolyl, isoxazolyl, or isothiazolyl;

or a pharmaceutically acceptable salt thereof, which are useful in treating metabolic disorders related to insulin resistance or hyperglycemia.

3 Claims, No Drawings

FURANS, BENZOFURANS, AND THIOPHENES USEFUL IN THE TREATMENT OF INSULIN RESISTANCE AND HYPERGLYCEMIA

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglyceriaa. The diabetic groups in these studies included both insulin dependent (EDDM) and noninsulin dependent (NIEDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischernic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in Diabetes in America 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, Receptor 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

C. Goldenberg et al., *Eur. J. Med. Chem.—Chim. Ther.* 1977, 12(1), 81–86 and M. Descamps et al., (DE 2710047) disclosed compounds of formula A.

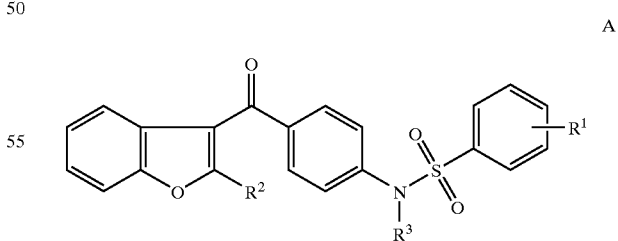

A $R^1$ is H, Cl, $NO_2$, $CH_3$, $OCH_3$ ; $R^2$ is alkyl; $R^3$ is H, alkylaminomethyl G. J. Cuilinan and K. J. Fahey (U.S. Pat. No. 5,596,106 A and WO 960201) disclose arylbenzo[b]thiophene and benzo[b]furan compounds B and C as cannabinoid receptor antagonists.

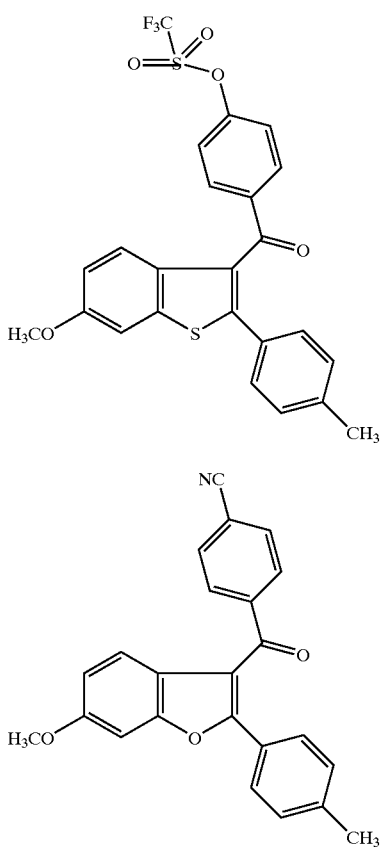

B

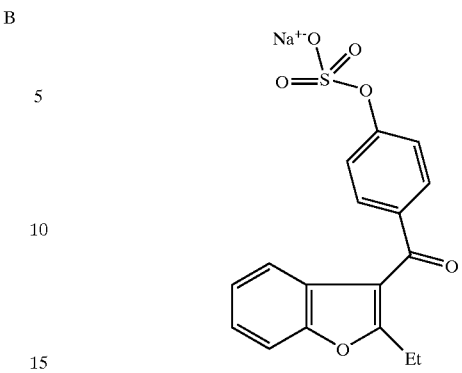

E

None of the above disclosures (A–E) contained the appropriate substitution necessary for in vitro PTPase inhibition activity.

DESCRIPTION OF THE INVENTION

This invention provides a compound of formula I having the structure

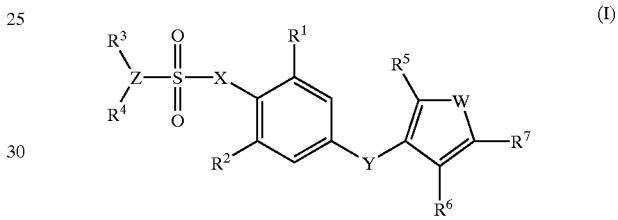

(I)

wherein $R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl substituted with trifluoromethyl, chloro, methoxy, or trifluoromethoxy;

$R^3$ and $R^4$ are each, independently, hydrogen, carboxy, hydroxy, hydoxyalkyl of 1–6 carbon atoms, alkoxy of 1–6 carbon atoms, perfluoroalkoxy of 1–6 carbon atoms, alkanoyloxy of 2–7 carbon atoms, perfluoroalkanoyloxy of 2–7 carbon atoms, arylalkoxy of 7–15 carbon atoms, aryloxy of 6–12 carbon atoms, aroyloxy of 7–13 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, alkylamino of 1–6 carbon atoms, dialkylamino of 1–6 carbon atoms per alkyl group, tetrazolyl, mercapto, nitrile, nitro, amino, —NHSO$_2$CF$_3$, carbamoyl, formyl, halogen, acylamino, 3-hydroxy-cyclobut-3-ene-4-yl-1,2-dione, or tetronic acid;

$R^5$ is hydrogen, alkyl of 1–6 carbon atoms, perfluoroalkyl of 1–6 carbon atoms, naphthalenylmethyl, benzyl or benzyl substituted with halogen, $R^6$ and $R^7$ are each, independently, hydrogen, alkyl of 1–6 carbon atoms, or perfluoroaLkyl of 1–6 carbon atoms, or $R^6$ and $R^7$ may be taken together as a diene unit having the structure —CH=CH—CH=CH—;

W is S or O,

X is —NR$^8$CH$_2$—, —NR$^8$—, or O;

$R^8$ is hydrogen or alkyl of 1–6 carbon atoms;

Y is carbonyl, methylene, —CH$_2$CH$_2$—, or —NHCH$_2$—;

Z is phenyl, pyridyl, naphthyl, thienyl, furyl, pyrrolyl, pyrazolyl, isoxazolyl, or isothiazolyl;

or a pharmaceutically acceptable salt thereof, which are useful in treating metabolic disorders related to insulin resistance or hyperglycemia.

H. Grote (DE 3342624 A1) disclose Benzarone derivatives D for treating venous and arterial ailments.

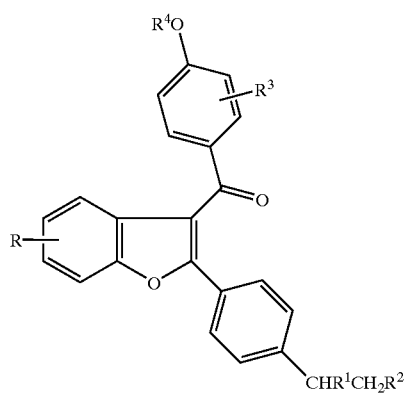

D (R, $R^1$, $R^2$ and $R^3$ is H, alkoxy, acyloxy, OH, SO$_3$H; $R^4$ is H, acyl, HSO$_2$)

T. Eckert (DE 3110460 and Arch. Pharm. (Weinheim, Ger.) 1982, 315(6), 569–570 discloses sodium benzaron sulfate E.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Alkyl includes both straight chain as well as branched moieties. Halogen means bromine, chlorine, fluorine, and iodine. It is preferred that the aryl portion of the aryl, arylkyl, arylalkoxy, aryloxy, aroyloxy, or aryloxycarbonyl substituent is a phenyl, naphthyl or 1,4-benzodioxan-5-yl group, with phenyl being most preferred. The aryl moiety may be optionally mono-, di-, or tri-substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —$CO_2H$, alkanoyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers, as well as the racemic and resolved, enantiomerically pure R and S stereoisomers, as well as other mixtures of the R and S stereoisomers and pharmaceutically acceptable salts thereof.

Preferred compounds of this invention are those compounds of Formula I,
wherein
$R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl substituted with trifluoromethyl, chioro, methoxy, or trifluoromethoxy;
$R^3$ and $R^4$ are each, independently, hydrogen, carboxy, hydroxy, alkoxy of 1–6 carbon atoms, perfluoroalkoxy of 1–6 carbon atoms, alkanoyloxy of 2–7 carbon atoms, perfluoroalkanoyloxy of 2–7 carbon atoms, aroyloxy of 7–13 carbon atoms, alkoxycarbonyl of 2–7 carbon atoms, aryloxycarbonyl of 7–13 carbon atoms, alkyl of 1–6 carbon atoms, perfluoroalkyl of 1–6 carbon atoms, tetrazolyl, mercapto, nitrile, amino, —$NHSO_2CF_3$, carbamoyl, formyl, acylamino of 2–7 carbon atoms;
$R^5$ is hydrogen, alkyl of 1–6 carbon atoms, naphthalenylmethyl, benzyl or benzyl substituted with halogen;
$R^6$ and $R^7$ are each, independently hydrogen or alkyl of 1–6 carbon atoms or $R^6$ and $R^7$ may be taken together as a diene unit having the structure —CH=CH—CH=CH—;
W is S or O,
X is —$NHCH_2$—, or O;
Y is carbonyl, methylene, —$CH_2CH_2$—, or —$NHCH_2$—;
Z is phenyl, pyridyl, naphthyl, thienyl, furyl, pyrrolyl, pyrazolyl, isoxazolyl, or isothiazolyl;
or a pharmaceutically acceptable salt thereof.

More preferred compounds of this invention are those compounds of Formula I,
wherein
$R^1$ and $R^2$ are each, independently, hydrogen, iodo, phenyl, thienyl, alkyl of 1–6 carbon atoms, bromo, or cycloalkyl of 3–8 carbon atoms, $R^3$ and $R^4$ are each, independently, hydrogen, carboxy, hydroxy, methyl, or acetoxy;
$R^5$ is hydrogen, alkyl of 1–6 carbon atoms, naphthalenylmethyl, benzyl or benzyl substituted with bromine;
$R^6$ and $R^7$ are each, independently, hydrogen or methyl, or $R^6$ and $R^7$ may be taken together as a diene unit having the structure —CH=CH—CH=CH—;
W is S or O,
X is —$NHCH_2$—, or O;
Y is carbonyl, methylene, —$CH_2CH_2$—, —$NHCH_2$—;
Z is phenyl, or pyrazolyl;
or a pharmaceutically acceptable salt thereof.

Specifically preferred compounds of the present invention are set forth below:

4-[2,6-Dibromo-4-(2-ethyl-benzofuran-3-carbonyl)-phenoxysulfonyl]-2-hydroxy-benzoic acid or a pharmaceutically acceptable salt thereof.

4-[5'-(2-Butyl-benzofuran-3-carbonyl)-[1,1'; 3'1"]terphenyl-2'-yloxysulfonyl]-2-hydroxy-benzoic acid or a pharmaceutically acceptable salt thereof.

4-[4-(2-Ethyl-benzofuran-3-carbonyl)-2,6-dimethyl-phenoxysulfonyl]-2-hydroxy-benzoic acid or a pharmaceutically acceptable salt thereof.

4-[4-(2-Ethyl-benzofuran-3-carbonyl)-2,6-diisopropyl-phenoxysulfonyll-2-hydroxy-benzoic acid or a pharmaceutically acceptable salt thereof.

4-[4-(2-Benzyl4,5-dimethyl-furan-3-carbonyl)-2,6-diisopropyl-phenoxysulfonyl]-2-hydroxy-benzoic acid or a pharmaceutically acceptable salt thereof.

4-[5'-(2-Ethyl-benzofuran-3-carbonyl)-[1,1'; 3',1"]terphenyl-2'-yloxysulfonyl]-2-hydroxy-benzoic acid or a pharmaceutically acceptable salt thereof.

4-[5-(2-Benzyl-4,5-dimethyl-furan-3-carbonyl)-3-methyl-biphenyl-2-yloxysulfonyl]-2-hydroxy-benzoic acid or a pharmaceutically acceptable salt thereof.

4-[4-(4,5-Dimethyl-2-naphthalen-2-ylmethyl-ftiran-3-carbonyl)-2,6-diisopropyl-phenoxysulfonyl]-2-hydroxy-benzoic acid or a pharmaceutically acceptable salt thereof.

4-{4-[2-(2-Bromo-benzyl)-4,5-dimethyl-furan-3-carbonyl]-2,6-diisopropyl-phenoxysulfonyl}-2-hydroxy-benzoic acid or a pharmaceutically acceptable salt thereof.

4-{4-[2-(3-Bromo-benzyl)-4,5-dimethyl-furan-3-carbonyl]-2,6-diisopropyl-phenoxysulfonyl}-2-hydroxy-benzoic acid or a pharmaceutically acceptable salt thereof.

4-{4-[2-(4-Bromo-benzyl)4,5-dimethyl-furan-3-carbonyl]-2,6-diisopropyl-phenoxysulfonyl}-2-hydroxy-benzoic acid or a pharmaceutically acceptable salt thereof.

2-Acetoxy-4-{4-[2-(2-Bromo-benzyl)-4,5-dimethyl-furan-3-carbonyl]-2-cyclopentyl-phenoxysulfonyl}-benzoic acid or a pharmaceutically acceptable salt thereof.

2-Acetoxy-4-{4-[2-(4-Bromo-benzyl)-4,5-dimethyl-thiophene-3-carbonyl]-2-cyclopentyl-phenoxysulfonyl}-benzoic acid or a pharmaceutically acceptable salt thereof.

2-Acetoxy4-[4-(2-benzyl-4,5-dimethyl-tbiophene-3-carbonyl)-2-cyclopentyl-phenoxysulfonyl]-benzoic acid or a pharmaceutically acceptable salt thereof.

2-Acetoxy-4-[4-(2-benzyl4,5-dimethyl-furan-3-carbonyl)-2-cyclopentyl-phenoxysulfonyl]-benzoic acid or a pharmaceutically acceptable salt thereof.

4-[4-(2-Benzyl-4,5-dimethyl-furan-3-carbonyl)-2,6-diethyl-phenoxysulfonyll-2-hydroxy-benzoic acid or a pharmaceutically acceptable salt thereof.

1-Methyl-1H-pyrazole-4-sulfonic acid 4-[2-(4-bromo-benzyl)-4,5-dimethyl-thiophene-3-carbonyl]-2-cyclopentyl-phenyl ester or a pharmaceutically acceptable salt thereof.

4-{4-[2-(2-Bromo-benzyl)-4,5-dimethyl-furan-3-carbonyl]-2-cyclopentyl-phenoxysulfonyl}-2-hydroxy-benzoic acid or a pharmaceutically acceptable salt thereof.

4-{4-[2-(4-Bromo-benzyl)-4,5-dirnethyl-thiophene-3-carbonyl]-2-cyclopentyl-phenoxysulfonyl}-2-hydroxy-benzoic acid or a pharmaceutically acceptable salt thereof.

4-[4-(2-Benzyl-4,5-dimethyl-thiophene-3-carbonyl)-2-cyclopentyl-phenoxysulfonyl]-2-hydroxy-benzoic acid or a pharmaceutically acceptable salt thereof.

4-[4-(2-Benzyl-4,5-dimethyl-furan-3-carbonyl)-2-cyclopentyl-phenoxysulfonyl]-2-hydroxy-benzoic acid or a pharmaceutically acceptable salt thereof.

4-{4-[2-(4-Bromo-benzyl)-4,5-dimethyl-furan-3-carbonyl]-2-cyclopentyl-phenoxysulfonyl}-2-hydroxy-benzoic acid or a pharmaceutically acceptable salt thereof.

4-[4-(2-Butyl-benzofuran-3-ylmethyl)-phenoxysulfonyl]-2-hydroxy-benzoic acid or a pharmaceutically acceptable salt thereof 4-[4-(2-Butyl-benzofuran-3-carbonyl)-phenoxysulfonyl]-2-hydroxy-benzoic acid or a pharmaceutically acceptable salt thereof.

4-{4-[2-(2-Butyl-benzofuran-3-yl)-ethyl]-phenoxysulfonyl}-2-hydroxy-benzoic acid or a pharmaceutically acceptable salt thereof.

2-Acetoxy4-{4-[2-(2-butyl-benzofuran-3-yl)-ethyl]-phenoxysulfonyl}-benzoic acid or a pharmaceutically acceptable salt thereof.

4-{4-[(2-Butyl-benzofuran-3-ylmethyl)-arnino]-phenoxysulfonyl}-2-hydroxy-benzoic acid or a pharmaceutically acceptable salt thereof.

4-{4-[2-(2-Benzyl-benzo[b]thiophen-3-yl)thyl]-phenoxysulfonyl}-2-hydroxy-benzoic acid or a pharmaceutically acceptable salt thereof.

The compounds of this invention were be prepared according to the following schemes from commercially available starting materials or starting materials which can be prepared using to literature procedures. These schemes show the preparation of representative compounds of this invention.

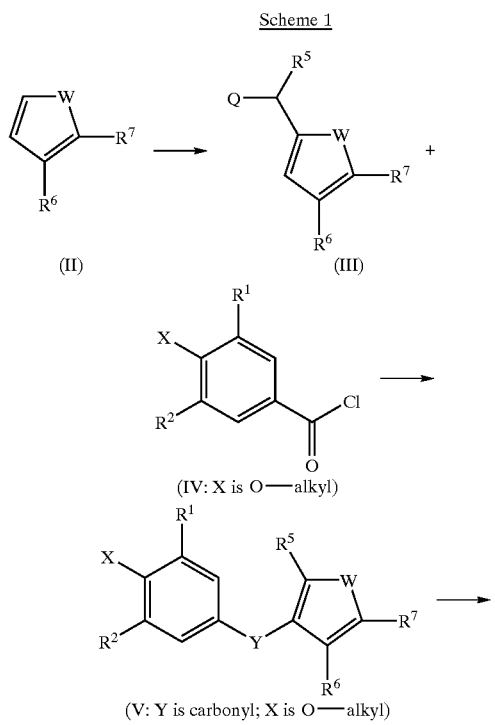

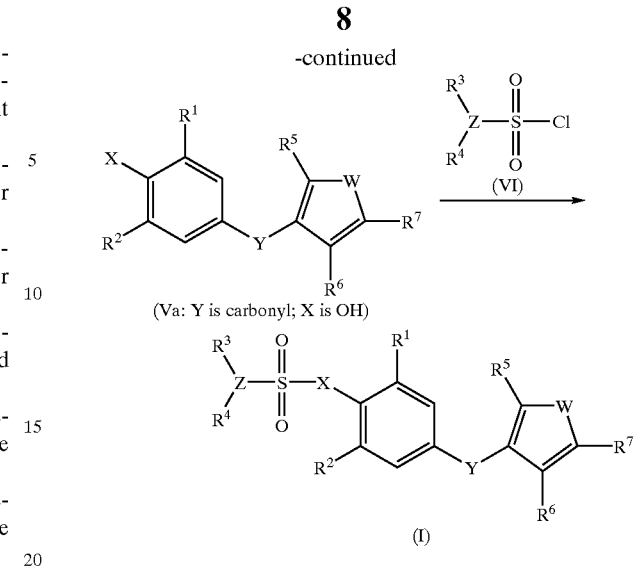

In Scheme 1, 2, 3-dimethylthiophene (II: W is S) is prepared from commercially available 3-methyl-thiophene-carboxaldehyde using Wolff-Kishner conditions (hydrazine followed by KOHiethylene glycol reflux). Compound (U) is treated with one to 1.3 molar equivalents of an alkyl lithium reagent such as N-butyl lithium most preferably in a non-protic solvent such as THF at temperatures ranging from −78° C. to room temperature under an inert atmosphere such as nitrogen or argon to provide the 2-lithiated-thiophene or furan derivative. This lithiated analog is reacted in situ with one or more molar equivalents of benzaldehyde, generally at −78° C. to room temperature for 5 min to 3 h to provide the compound of formula (III: Q is OH). The hydroxy group of (III: Q is OH) can be removed by a number of reduction procedures such as hydrogenation using palladium catalysts to produce the compound of formula (III: Q is H) but is most conveniently removed using the method of Nutaitis, et. al. (Org. Prep. and Proceed. Int. 1991, 23, 403–411) in which (III: Q is OH; W is S or O) is stirred with one to ten molar equivalents of sodium borohydride in a suitable solvent such as ether, THF or dichioromethane at 0° C. to room temperature and one to fifty molar equivalents of trifluoroacetic acid is slowly added over a 15 min to 3 h period to produce the compound of formula (III: Q is H). Alternatively, the 2-lithiated analog of compound (II) in a nonprotic solvent such as THF can be reacted with one or more molar equivalents of a benzyl halide such as benzyl bromide (PhCH$_2$Br) at −78° C. to room temperature to directly provide the compound of formula (III: Q is H; W is S or O).

The compounds of formula (III: Q is H) can be acylated with one or more molar equivalents of a commercially available benzoic acid chloride of formula (IV: X is O-alkyl) to produce the acylated derivative of formula (V: X is O-alkyl). This acylation is accomplished most readily using a one to five molar equivalents of a Lewis acid catalyst such as tin tetrachloride or aluminum chloride in an inert solvent such as dichioromethane, 1,2-dichloroethane or carbon disulfide, generally at temperatures such as −78° C. to room temperature. The benzoic acid chloride (IV: X is —O-alkyl). is prepared from the corresponding benzoic acid by standard procedures using reagents such as oxalyl chloride and thionyl chloride. The starting benzoic acid of the benzoic acid chloride (IV: X is O-alkyl) is commercially available or can be easily prepared by known procedures For example, the acid starting material for benzoic acid chloride (IV) can be prepared using a modification of the method of Schuster, et al., J. Org. Chem. 1988, 53, 5819. Thus commercially available 2, 6-diisopropyl phenol is brominated in the 4-position (bromine/acetic acid), methylated (iodomethane/potassium carbonate/DMF), reacted with n-butyl lithium to effect lithium halogen exchange and the resultant organolithium species is reacted with carbon dioxide to provide 3,5-diisopropyl, 4-methoxy benzoic acid. Alternatively, the commercially available 2,6-(mono or disubstituted)phenols can be methylated (iodomethane/potassium carbonate/DMF), acylated in the 4-position with 2-chlorobenzoyl chloride in the presence of aluminum chloride in an inert solvent such as dichloromethane, generally at ambient temperature and reacted with potassium-t-butoxide in $H_2O$/ethylene glycol dimethyl ether at ambient temperature to give the desired 2,6-(mono or disubstituted)benzoic acid.

The conversion of the alkyl ether compound (V: X is O-alkyl) to the phenol compound (Va: X is OH) is generally best accomplished using one to ten molar equivalents of a strong Lewis acid such as a trihaloborane, most conveniently tribromoborane. The reaction is best performed at −78° C. with warming to 0° C.

The compounds of formula (Va: X is OH) can be sulfonylated on the phenolic oxygen using one or more molar equivalents of suitable sulfonylating agent (VI) to provide the sulfonic acid esters of formula (I: Y is carbonyl). The sulfonylating agent (VI) is generally a aryl or heteroaryl sulfonic acid chloride. The reaction is run under standard conditions using a suitable base such sodium hydride, pyridine or Tris base in an appropriate solvent such as dichloromethane, THF or $H_2O$ at temperatures from 0° C. to ambient temperature. The starting aryl or heteroaryl sulfonic acid chloride is commercially available or can be easily prepared by known procedures. The aryl or heteroaryl sulfonic acid chloride can be prepared by reacting the aryl or heteroaryl sulfonic acid with one or more molar equivalents of oxalyl chloride or thionyl chloride, in a suitable solvent such as dichloromethane, chloroform or diethyl ether, to afford the aryl or heteroaryl sulfonic acid chloride. This reaction is often catalyzed by adding small amounts (0.01 to 0.1 molar equivalents) of dimethylformamide. Alternatively, the aryl or heteroaryl sulfonic acid chloride can prepared using a modification of Barraclough, et al., *Arch. Pharm.* (Weinheim) 1990, 323, 507. Thus, the aniline of commercially available 4-aminosalicylic acid sodium salt dihydrate is diazotized with sodium nitrite in HOAc/HCl at −10° C. and the subsequent the diazonium salt can converted to the sulfonyl chloride by introduction of sulfur dioxide into the reaction in the presence of copper (I) chloride.

The groups $R^3$ and $R^4$ connected to Z can be further derivatized. For example, when $R^3$ or $R^4$ is an ester of a carboxylic acid or alcohol the compound can be transformed into the respective carboxylic acid or alcohol analog using standard conditions. The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. When $R^3$ or $R^4$ is a carboxylic acid or ester the compound can be reduced to the respective primary alcohol analog using standard conditions such as lithium aluminum hydride in ethyl ether. When $R^3$ or $R^4$ is an aldehyde or ketone the compound can be reduced to the respective primary alcohol analog using a metal catalyst, by sodium in alcohol, sodium borohydride and by lithium aluminum hydride. When $R^3$ or $R^4$ is an ether, the compound can be transformed to the free alcohol by using one to ten molar equivalents of a strong Lewis acid such as a trihaloborane, most conveniently tribromoborane in a halocarbon solvent such as dichloromethane. When $R^3$ or $R^4$ is an alcohol the compound can be oxidized to the respective aldehyde, carboxylic acid or ketone analog using a transition metal oxidant (chromium trioxide-pyridine, pyridinium chlorochromate, manganese dioxide) in an inert solvent such as ether, dichloromethane. Alcohols can also be oxidized using DMSO with a number of electrophilic molecules (dicyclohexylcarbodiimide, acetic anhydride, trifluoro acetic anhydride, oxalyl chloride and sulfur dioxide). When $R^3$ or $R^4$ is a carboxylic acid the compound can be transformed into a carboxylic acid amide analog. This transformation can be accomplished using standard methods to effect carboxylic acid to carboxylic acid amide transformations. These methods include converting the acid to an activated acid and reacting with one or more molar equivalents of the desired amine. Amines in this category include ammonia in the form of ammonium hydroxide, hydroxyl amine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C. When $R^3$ or $R^4$ is nitro, the compound can be reduced to the respective amino compound most readily using tin dichloride in ethylacetate at 40 to 100° C. or with hydrazine and Montmorillnite clay in ethanol at 40 to 100° C. or by catalytic hydrogenation in the presence of a catalyst such as palladium on carbon. When $R^3$ or $R^4$ is an amino or an alcohol, the compound can be acylated using one or more molar equivalents of suitable acylating agent. The acylating agent is generally a lower alkyl or aryl carboxylic acid anhydride or a lower alkyl or aryl carboxylic acid chloride. The reaction is run under standard conditions, for example the use of pyridine as solvent with or without a co-solvent such as dichloromethane at 0° C. to room temperature. When $R^3$ or $R^4$ is an alcohol it can be acylated with a lower alkyl or aryl carboxylic acid anhydride in the presence of magnesium iodide in diethyl ether at ambient temperature to reflux. When $R^3$ or $R^4$ is a nitrile it can be reduced to the aminoalkyl compound by tin (II) chloride in refluxing ethyl acetate or by catalytic hydrogenation in the presence of a catalyst such as Raney nickel or by lithium aluminum hydride in an inert solvent such as ether. When $R^3$ or $R^4$ is a nitrile it can be converted to a carboxylic acid amide using standard conditions such as HCl/$H_2O$ at ambient temperatures to reflux or a milder procedure involves the reaction of the nitrile with an alkaline solution of hydrogen peroxide. When $R^3$ or $R^4$ is halogen or trifluoromethanesulfonate it can be converted to a 3-hydroxy-cyclobut-3-ene-4-yl-1,2-dione by methodology of Liebeskind et. al. (*J. Org. Chem.* 1990, 55, 5359). When $R^3$ or $R^4$ is an alcohol can be alkylated with a suitable alkylating agent such as one or more molar equivalents of alkyl halide in the presence a base such as potassium carbonate or sodium hydroxide in a suitable solvent such as TBF, DMF or DMSO at temperatures ranging from 0° C. to 60° C. When $R^3$ or $R^4$ is a carboxylic acid, the compound can be coupled to tetronic acid with a coupling reagent such as 1-(3-dimethylaminopropyl)-3-ethylcarbodiimide in the presence of a base such as triethylamine or DMAP in a suitable solvent such as DMF.

Scheme 2

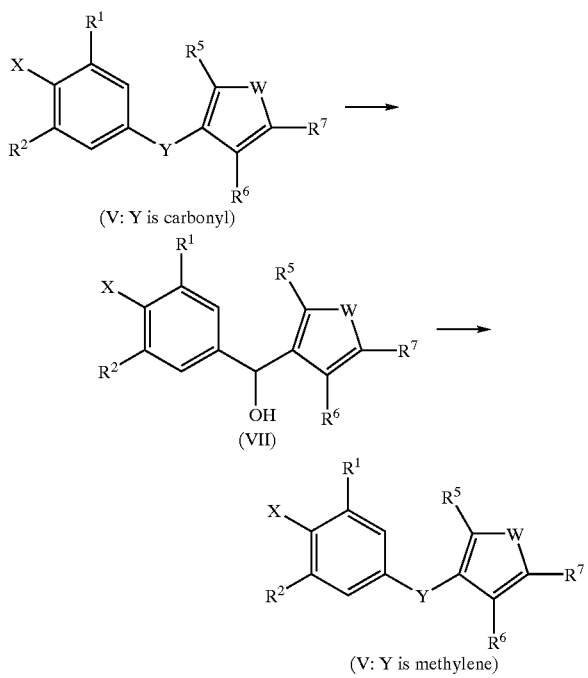

(V: Y is carbonyl)

(VII)

(V: Y is methylene)

The following method will prepare derivatives of formula (V: Y is methylene) that can utilized in Scheme 1 to prepare compounds of formula (I: Y is methylene). The ketone (V: Y is carbonyl) can be reduced with lithium aluminum hydride in an aprotic solvent such as THF at ambient temperature to give the alcohol (VII). Further reduction of alcohol (VII) with triethylsilane in the presence of boron trifluoride diethyl etherate provides the methylene compound (V: Y is methylene). The compounds prepared in Scheme 2 of formula (V: Y is methylene) can be further modified synthetically in Scheme 5.

Scheme 3

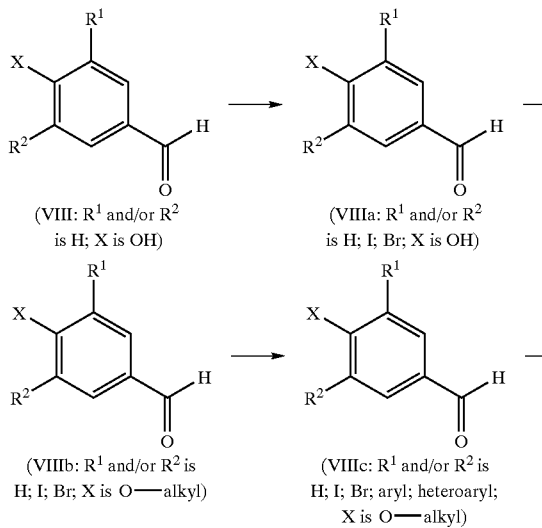

(VIII: $R^1$ and/or $R^2$ is H; X is OH)

(VIIIa: $R^1$ and/or $R^2$ is H; I; Br; X is OH)

(VIIIb: $R^1$ and/or $R^2$ is H; I; Br; X is O—alkyl)

(VIIIc: $R^1$ and/or $R^2$ is H; I; Br; aryl; heteroaryl; X is O—alkyl)

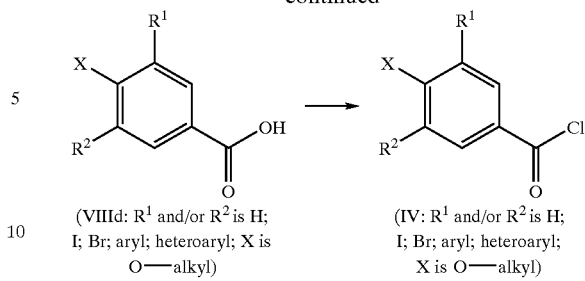

(VIIId: $R^1$ and/or $R^2$ is H; I; Br; aryl; heteroaryl; X is O—alkyl)

(IV: $R^1$ and/or $R^2$ is H; I; Br; aryl; heteroaryl; X is O—alkyl)

Derivatives of formula (IV: $R^1$ and/or $R^2$ is H; I; Br; aryl; heteroaryl; X is O-alkyl) can be prepared according to Scheme 3. The p-hydroxybenzaldehyde (VIII) can be conveniently iodinated to the diiodophenol of formula (VIIIa: $R^1$ and $R^2$ is I) using at least two molar equivalents of iodine in the presence of two or more molar equivalents of an alkali metal hydroxide such as NaOH in an alcohol solvent such as methanol at −20° C. to room temperature. Similarly the monoiodophenol (VIIIa: $R^1$ is H; $R^2$ is I) can be prepared from the phenol of formula (VIII) using one to 1.5 molar equivalents of iodine in the presence of at least one equivalent of an alkali metal hydroxide such as NaOH in a alcohol solvent such as methanol at −20° C. to room temperature. Either the monoiodophenol (VIIIa: $R^1$ is H; $R^2$ is I) or the diiodophenol (VIIIa: $R^1$ and $R^2$ is I) can be converted to the respective alkyl ether derivatives of formula (VIIIb: $R^1$ is H; $R^2$ is I; X is —O-alkyl) or (VIIIb: $R^1$ and $R^2$ is I; X is —O-alkyl) by reacting the phenol moiety with a suitable alkylating agent such as one or more molar equivalents of methyl iodide or dimethylsulfate employing a base such an alkali methyl carbonate or hydroxide such as potassium carbonate or sodium hydroxide in a suitable solvent such as THF, DMFN or DMSO. The reaction is generally performed at temperatures ranging from 0° C. to 60° C. The mono or dibrominated benzaldehydes of formula (VIIIb: $R^1$ and/or $R^2$ is Br; X is —O-alkyl) can be prepared in analogs fashion by substituting bromine for iodine in the sequence above.

The mono or diiodo alkyl ether benzaldehydes of formula (VIIIb: $R^1$ and/or $R^2$ is I; X is O-alkyl) can be reacted with an arylboronic acid or heteroarylboronic acid to afford the product of formula (VIIIc: $R^1$ and/or $R^2$ is aryl or heteroaryl; X is —O-alkyl) under the conditions of the Suzuki Reaction (*Journal of the Chemical Society Chemical Communications* 1979 886 and *Synthetic Communications* 1981 11(7) 513). The other co-reagents necessary to effect the Suzuki Reaction include one or more molar equivalents of a metal catalyst such as tetrakis(triphenylphosphine)palladium or palladium (II) acetate and a base such as barium hydroxide octahydrate or sodium carbonate in a solvent such as benzene, toluene or DME/$H_2O$. The starting aryl or heteroaryl boronic acids are commercially available or can be prepared by standard synthetic methods.

The mono or diaryl or mono or diheteroaryl benzaldehyde analogs of formula (VIIIc: $R^1$ and/or $R^2$ is aryl or heteroaryl; X is —O-alkyl) can be converted to the corresponding mono or diaryl or mono or diheteroaryl benzoic acid analogs of formula (VIIId: $R^1$ and/or $R^2$ is aryl or heteroaryl; X is —O-alkyl) using the oxidative conditions of silver (I) oxide in an aqueous base such as sodium hydroxide at temperatures ranging from 50° C. to reflux.

The benzoic acid compound (VIII: $R^1$ and/or $R^2$ is H; I; Br; aryl; heteroaryl; X is O-alkyl) can be converted to the corresponding benzoic acid chloride (IV: $R^1$ and/or $R^2$ is H; I; Br; aryl heteroaryl; X is O-alkyl) by standard procedures using reagents such as oxalyl chloride and thionyl chloride. The compounds prepared in Scheme 3 of formula (IV: $R^1$ and/or $R^2$ is H; I; Br; aryl; heteroaryl; X is O-alkyl) can be utilized in Scheme-₁ to prepared compounds of formula (I: $R^1$ and/or $R^2$ is H; I; Br; aryl; heteroaryl).

Scheme 4

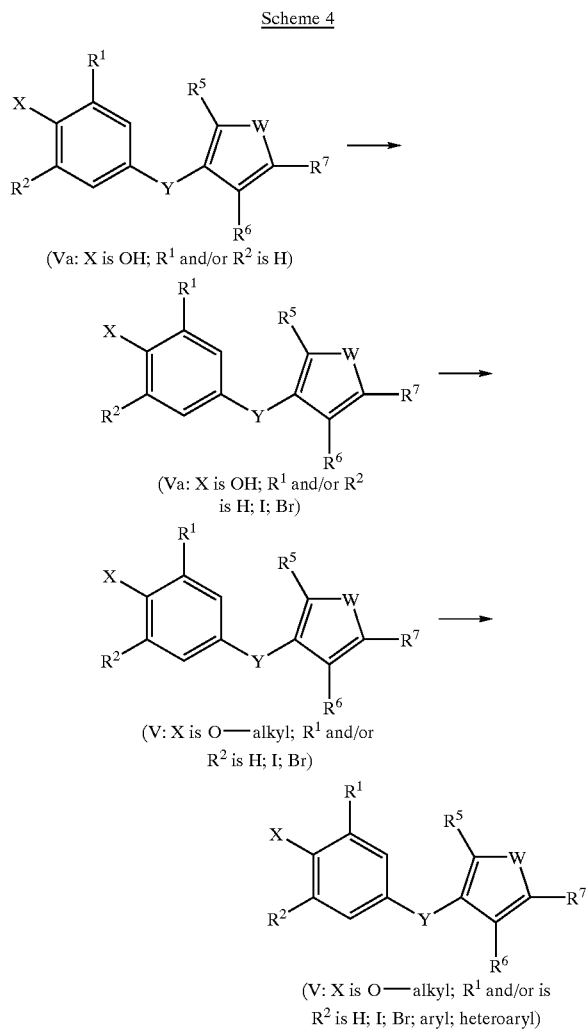

In an analogous synthetic sequence to Scheme 3, compounds of formula (Va: X is OH; $R^1$ and/or $R^2$ is H) can be functionalized at positions $R^1$ and $R^2$ to give compounds of formula (V: X is O-alkyl; $R^1$ and/or $R^2$ is H; I; Br; aryl; heteroaryl). The compounds prepared in Scheme 4 of formula (V: $R^1$ and/or $R^2$ is H; I; Br; aryl; heteroaryl; X is O-alkyl) can be utilized in Scheme 1 to prepared compounds of formula (I: $R^1$ and/or $R^2$ is H; I; Br; aryl; heteroaryl). The compounds prepared in Scheme 4 of formula (V: $R^1$ and/or $R^2$ is H; I; Br; aryl; heteroaryl; X is O-alkyl) can be synthetically modified in Scheme 5.

Scheme 5

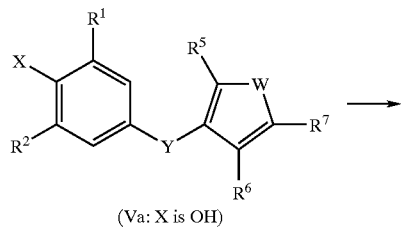

-continued

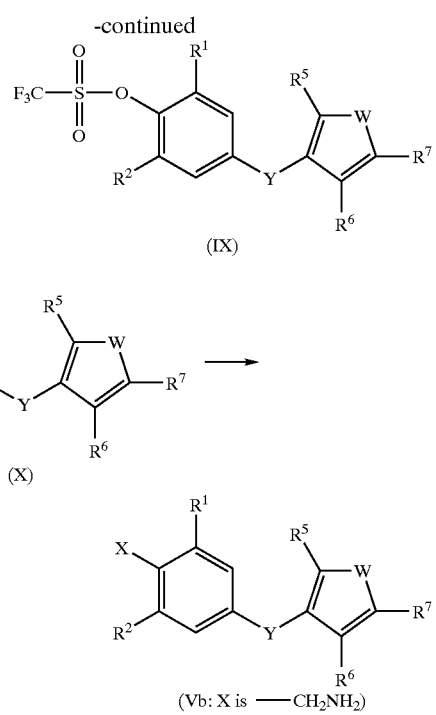

In a three step process (Scheme 5) compounds of formula (Va: X is OH) can be converted to compounds of formula (Vb: X is —CH₂NH₂). Reaction of compounds of formula (Va: X is OH) with trifluoromethanesulfonic anhydride or trifluoromethanesulfonic acid chloride in the presence of a organic base such as pyridine or triethylamine in dichloromethane at 0° C. to ambient temperature provides compound (IX). The triflate (IX) can be converted to the carbonitrile (X) with potassium cyanide or zinc cyanide in the presence of tetrakistriphenylphosphinenickel(0) which can be generated in situ from bistriphenylphosphinenickel (II) bromide and ZnPPh₃. The nitrile (X) can be reduced to the aminoalkyl compound (Vb: X is —CH₂NH₂) by tin (II) chloride in refluxing ethyl acetate or by catalytic hydrogenation in the presence of a catalyst such as Raney nickel or by lithium aluminum hydride in an inert solvent such as ether.

From Scheme 5, the prepared compounds of formula (Vb: X is —CH₂NH₂) can be used in Scheme 1 to prepared sulfonamides of formula (I: X is —CH₂NH—).

Scheme 6

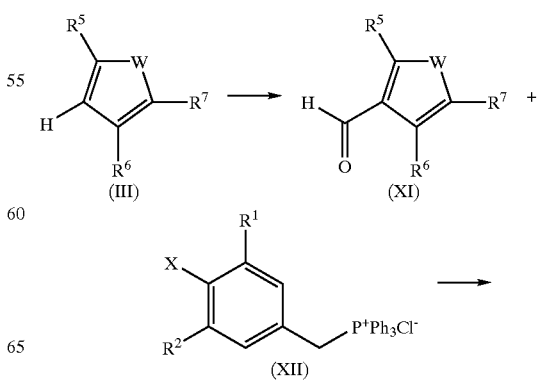

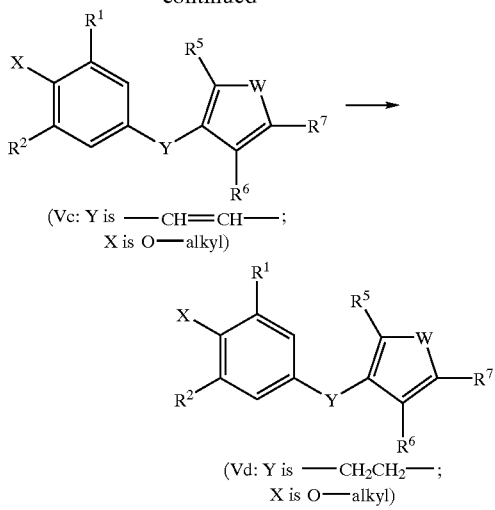

(Vc: Y is —CH=CH—;
X is O—alkyl)

(Vd: Y is —CH₂CH₂—;
X is O—alkyl)

In Scheme 6, the aldehyde (XI) can be prepared from commercially available furan (III: W is O ) using phosphorus oxychloride in dimethyl formaldehyde at 85° C. under an inert atmosphere. Compound (XI) is treated with one to 1.3 molar equivalents of an suitable Wittig reagent in a nonprotic solvent such as THF at temperatures ranging from −78° C. to room temperature under an inert atmosphere such as nitrogen or argon to provide the olefin derivative. The olefin (Vc: Y is —CH=CH—) can be converted to the alkane (Vd: Y is —CH₂CH₂—) through any standard procedure for hydrogenation. The most convenient method of reduction is catalytic hydrogenation employing 10% palladium on carbon over an atmosphere of hydrogen for 12–24 hours.

The compounds prepared in Scheme 6 of formula (Vc: Y is —CH=CH—) or (Vd: Y is —CH2CH2—) can be utilized in Scheme 1 to prepared compounds of formula (I: Y is —CH=CH— or —CH₂CH₂—). The compounds prepared in Scheme 6 can be synthetically modified in Schemes 4 and 5.

Scheme 7

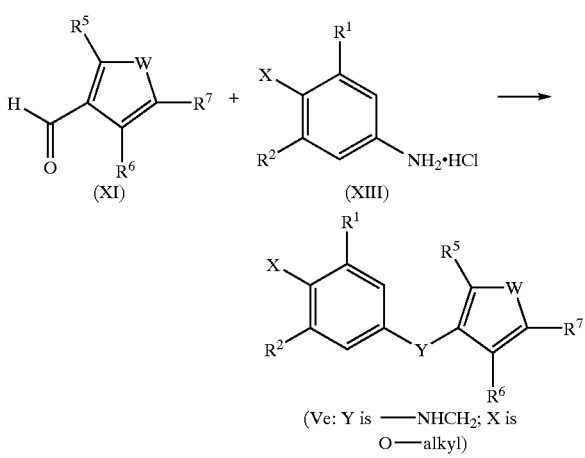

(Ve: Y is —NHCH₂; X is O—alkyl)

Compounds of formula (Ve: Y is —NHCH2—) in Scheme 7 can be prepared through a number of reductive amination procedures such as the method of Maryanoff, et. al. (*J. Org. Chem.* 1996, 61, 3849–62), but is easily prepared by a modified procedure of Borch, et. al. (*J. Am. Chem. Soc.* 1971, 93, 2897–04. A solution of the aldehyde (XI) (as prepared in Scheme 6), and the appropriate aniline hydrochloride (XIII) (1.2–1.5 equivalent) in a suitable protic solvent such as methanol is stirred at room temperature in the presence of sodium cyanoborohydride (1.1–1.5 equivalent) yields compounds of formula (Ve: Y is —NHCH2—).

The compounds prepared in Scheme 7 of formula (Ve: Y is —NHCH2—) can be utilized in Scheme 1 to prepared compounds of formula (I: Y is —NHCH2—). The compounds prepared in Scheme 6 can be synthetically modified in Schemes 4 and 5.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedure which measures the inhibition of PTPase.
Inhibition of Tri-Phosphorylated Insulin Receptor Dodecaphosphopeptide Dephosphorylation by hPTP 1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell Biochem.* 109, 107, 1992). The enzyme preparation used was in microtubes containing 500–700 μg/ml protein in 33 mM Tris-HCl, 2 mM EDTA, 10% glycerol and 10 mM 2-mercaptoethanol. Measurement of PTPase activity.

The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.), the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 rnM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.51 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AMJFw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.

Calculations:

PTPase activities, based on a potassium phosphate standard curve, are expresses as nmoles of phosphate released/min/mg protein, inhibition of recombinant PTP1B by test compounds is calculated as percent of phosphatase control. A four parameter non-linear logistic regression of PTPase activities using SAS release 6.08, PROC NLIN, is used for determining $IC_{50}$ values of test compounds. The following results were obtained.

| Example | IC50 ($\mu$M) |
| --- | --- |
| 1 | 0.251 |
| 2 | 0.130 |
| 3 | 0.421 |
| 4 | 0.559 |
| 5 | 0.083 |
| 6 | 0.256 |
| 7 | 0.180 |
| 8 | 0.075 |
| 9 | 0.083 |
| 10 | 0.226 |
| 11 | 0.099 |
| 12 | 0.183 |
| 13 | 0.267 |
| 14 | 0.060 |
| 15 | 28.78% inhibition @ 1.0 $\mu$M |
| 16 | 22.81% inhibition @ 0.5 $\mu$M |
| 17 | 0.643 |
| 18 | 0.404 |
| 19 | 0.633 |
| 20 | 0.148 |
| 21 | 0.371 |
| 22 | 0.508 |
| 23 | 0.439 |
| 24 | 0.254 |
| 25 | 0.241 |
| 26 | 51.37% inhibition @ 1.0 $\mu$M |
| 27 | 22.69% inhibition @ 1.0 $\mu$M |
| 28 | 0.577 |
| Phenylarsine oxide (reference standard) | 39.7 |
| Sodium orthovanadate (reference standard) | 244.8 |
| Ammonium molybdate tetrahydrate (reference standard) | 8.7 |

Based on the results obtained in the standard pharmacological test procedure, representative compounds of this invention have been shown to inhibit PTPase activity and are therefore useful in treating metabolic disorders related to insulin resistance or hyperglycemia, typically associated with obesity or glucose intolerance. More is invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal admininistrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

4-[2,6-Dibromo-4-(2-ethyl-benzofuran-3-carbonyl)-phenoxysulfonyl]-2-hydroxy-benzoic acid Step 1

4-Chlorosulphonyl-2-hydroxybenzoic acid

At ambient temperature, to a stirred solution of commercial 4-aminosalicylic acid sodium salt dihydrate (50.25 g, 0.2379 mol) in $H_2O$ (119 mL) was added a solution of 10% aq. NaOH (3.40 mL) and sodium nitrite (18.06 g, 0.2617 mol) in $H_2O$ (44 mL). This solution was added to a vigorously stirred mixture of conc. HCL (153 mL) and glacial HOAc (76 mL) while maintaining the reaction temperature at −10 ° C. After 5 min., the dark orange suspension was added to a vigorously stirred mixture of copper (I) chloride (2.355 g, 0.02379 mol) in HOAc (128 mL) which had been previously cooled to 0° C. The reaction was saturated with sulfur dioxide for 0.5 h. The ice bath was removed and the reaction was stirred for 18 h. The reaction was quenched into crushed ice (2 L), allowed to warm to ambient temperature and filtered. The crude product was slurried in 20% THF/ether (1 L), dried ($MgSO_4$), filtered and concentrated to give 36.32 g (64%) of the title compound as a red solid, mp 170–185° C.; $^1$H NMR (DMSO-d6) δ7.11–7.16 (m, 2 H), 7.76 (d, 1 H), 13.2–14.4 (br. s, 2 H).

Step 2

4-[2,6-Dibromo4-(2-ethyl-benzofuran-3-carbonyl)-phenoxysulfonyl]-2-hydroxy-benzoic acid At ambient temperature, to a stirred solution of commercial benzbromarone (0.243 g, 0.574 mmol) in 0.5M aq. NaHCO$_3$:THF (8 mL; 1:1) was added portionwise 4-chlorosulphonyl-2-hydroxybenzoic acid (0.271 g, 1.15 mmol) while maintaining the pH at 8 with the simultaneous addition of 0.5M aq. NaHCO$_3$. After the addition was complete the reaction was stirred for 18 h. To the reaction was added 4-chlorosulphonyl-2-hydroxybenzoic acid (0.271 g, 1.15 mmol) while maintaining the pH at 8 with the simultaneous addition of 0.5M aq. NaHCO$_3$. After 2 h, the reaction was quenched with 2N HCl (25 mL), extracted with EtOAc and concentrated. The crude product was purified by preparative HPLC (C18, eluting with 75% CH$_3$CN/H20 containing 0.1% TFA) and crystallized from EtOAc/hexane to give 0.14 g (39%) of the title compound as a white solid, mp 173° C.; $^1$H NMR (DMSO-d6) δ1.25 (t, 3 H), 2.76 (q, 2 H), 7.30 (dt, 1 H), 7.36 (dt, 1 H), 7.44–7.49 (m, 3 H), 7.66 (d, 1 H), 8.03 (d, 1 H), 8.08 (s, 2 H). IR (KBr) 3400, 2950, 1680, 1650, 1400 and 1180 cm$^{-1}$. mass spectrum (–ESI), m/z 621/623/625 (M–H). Anal. Calcd. for C$_{24}$H$_{16}$Br$_2$O$_8$S: C, 46.18; H, 2.58; N, 0.00. Found: C, 46.41; H, 2.64; N, 0.00.

EXAMPLE 2

4-[5'-(2-Butyl-benzofuran-3-carbonyl)-[1,1'; 3'1"]terphenyl-2'-yloxysulfonyl]-2-hydroxy-benzoic acid Step 1

2-n-Butyl-3-(4-hydroxy-3,5-diiodobenzoyl)benzofuran

At 0° C., to a stirred solution containing commercial 2-n-butyl-3-(4-hydroxybenzoyl)benzofuran (1.05 g, 3.57 mmol) and sodium hydroxide (0.286 g, 7.14 mmol) in MeOH (35.7 mL) was added iodine (2.27 g, 8.93 mmol). After 24h, the reaction was quenched with 1N HCl (30 mL) and extracted with ether. The combined ethereal extracts were washed with 10% aq. Na$_2$S$_2$O$_3$ (3×), with brine (3×), dried (MgSO$_4$) and concentrated. The crude product was purified on Biotage KP-Sil to give 0.914 g (47%) of the title compound. $^1$H NMR (DMSO-d6) δ0.85 (t, 3 H), 1.27 (sextet, 2 H), 1.71 (quintet, 2 H), 2.77 (t, 2 H), 7.29–7.36 (m, 2 H), 7.45 (d, 1 H), 7.65 (d, 1 H), 8.11 (s, 2 H), 10.5 (br s, 1 H).

Step 2

2-n-Butyl-3-(4-[(2-methoxyethoxy)methoxy]-3,5-diiodobenzoyl)benzofuran

At 0° C., to a stirred solution of 2-n-butyl-3-(4-hydroxy-3,5-diiodobenzoyl)benzofuran (0.897 g, 1.64 mmol) in THF (16.4 m) was added 60% NaH/mineral oil (85.4 mg, 2.14 mmol). After 0.5 h, to the reaction was added MEM chloride (0.301 mL, 2.63 mmol) and the reaction was stirred for 18 h eventually warming to ambient temperature. The reaction was quenched with 1N NaOH (30 mL) and extracted with ether. The ethereal extracts were washed with 1N NaOH (3×), with brine (3×), dried (K$_2$CO$_3$) and concentrated to give 1.042 g (100%) of the title compound. $^1$H NMR (DMSO-d6) δ0.85 (t, 3 H), 1.26 (sextet, 2 H), 1.70 (quintet, 2 H), 2.74 (t, 2 H), 3.28 (s, 3 H), 3.56 (t, 2 H), 4.03 (t, 2 H), 5.26 (s, 2 H), 7.28–7.40 (m, 2 H), 7.49 (d, 1 H), 7.66 (d, 1 H), 8.18 (s, 2 H).

Step 3

(2-n-Butyl-benzofuran-3-yl)-(2'-[(2-methoxyethoxy)methoxy]-[1,1'; 3',1"]terphenyl-5'-yl)-methanone At ambient temperature, to a stirred mixture containing phenylboronic acid (0.454 g, 3.73 mmol), barium hydroxide octahydrate (1.60 g, 5.08 mmol) and palladium (II) acetate (7.60 mg, 0.0339 mmol) in DME:H$_2$O (6:1, 20 mL) was added a solution of 2-n-butyl-3-(4-[(2-methoxyethoxy)methoxy]-3,5-diiodobenzoyl)benzofuran (1.07 g, 1.69 mmol) in DME:H$_2$O (6:1, 20 mL). After the addition was complete, the reaction was heated at 80° C. for 16h. The reaction was cooled to ambient temperature, diluted with ether (50 mL), washed sequentially with sat. aq. NaHCO$_3$ (3×), with brine (3×), dried (MgSO$_4$) and concentrated. The crude product was purified on Biotage KP-Sil eluting with 25% ether/pet. ether to give 0.380 g (42%) of the title compound. $^1$H NMR (DMSO-d6) δ0.76 (t, 3 H), 1.22 (sextet, 2 H), 1.64 (quintet, 2 H), 2.81–2.92 (m, 6 H), 3.03 (s, 3 H), 4.44 (s, 2 H), 7.31–7.67 (m, 14 H), 7.76 (s, 2 H).

Step 4

(2-n-Butyl-benzofuran-3-yl)-(2'-hydroxy-[1,1: 3',1"]terphenyl-5'-yl)-methanone

At ambient temperature, to a stirred solution of (2-n-butyl-benzofuran-3-yl)-(2'-[(2-methoxyethoxy)methoxy]-[1,1';3',1"]terphenyl-5'-yl)-methanone (0.371 g, 0.695 mmol) in CH$_2$Cl$_2$ (3.71 mL) was added trifluoroacetic acid (3.71 mL). After 0.5h, the reaction was diluted with ether (50 mL), washed with H20 (3×), dried (MgSO$_4$) and concentrated. The crude product was purified on Biotage KP-Sil eluting with 10% acetone/hexane to give 0.281 g (90%) of the title compound. $^1$H NM (DMSO-d6) δ0.77 (t, 3 H), 1.22 (sextet, 2 H), 1.64 (quintet, 2 H), 2.87 (t, 2 H), 7.29–7.65 (m, 14 H), 7.66 (s, 2 H), 9.39 (s, 1 H).

Step 5

4-[5'-(2-Butyl-benzofuran-3-carbonyl)-[1,1'; 3'1"]terphenyl-2'-yloxysulfonyl]-2-hydroxy-benzoic acid The title compound was prepared according to the procedure in Example 1, step 2, using (2-n-butyl-benzofuran-3-yl)-(2'-hydroxy-[1,1';3 ',1"]terphenyl-5'-yl)-methanone (0.136 g, 0.305 mmol) and 4-chlorosulphonyl-2-hydroxybenzoic acid (0.144 g, 6.09 mmol) to give 0.080 g (38%) of the title compound as a white solid, mp 190–197° C.; $^1$H NMR (DMSO-d6) δ0.77 (t, 3 H), 1.22 (sextet, 2 H), 1.63 (quintet, 2 H), 2.83 (t, 2 H), 6.55 (d, 1 H), 6.66 (dd, 1 H), 7.28–7.38 (m, 8 H), 7.41-7.43 (m, 4 H), 7.51 (dd, 1 H), 7.57 (d, 1 H), 7.64 (d, 1 H), 7.74 (s, 2 H). IR (KBr) 2900, 1675, 1390 and 1190 cm$^{-1}$. mass spectrum (–ESI), mlz 645 (M–H). Anal. Calcd. for C$_{38}$H$_{30}$O$_8$S.2H$_2$O: C, 66.85; H, 5.02; N, 0.00. Found: C, 66.80; H, 4.88; N.0.07.

EXAMPLE 3

4-[4-(2-Ethyl-benzofuran-3-carbonyl)-2,6-dimethyl-phenoxysulfonyl]-2-hydroxy-benzoic acid The title compound was prepared according to the procedure in Example 1, step 2, using 2-n-ethyl-3-(4-hydroxy-3,5-dimethylbenzoyl)benzofuran (0.250 g, 0.849 mmol, RN 52489-58-4) and 4-chlorosulphonyl-2-hydroxybenzoic acid (0.402 g, 1.70 mmol) to give 0.15 g (36%) of the title compound as a white solid, mp 166–167° C.; $^1$H NMR (DMSO-d6) δ1.24 (t, 3 H), 2.14 (s, 6 H), 2.74 (q, 2 H), 7.30 (dt, 1 H), 7.36 (dt, 1 H), 7.44–7.48 (m, 3 H), 7.57 (s, 2 H), 7.66 (d, 1 H), 8.05 (d, 1 H). IR (KBr) 3400, 2950, 1680, 1650 and 1180 cm$^{-1}$. mass spectrum (–ESI), m/z 493 (M–H). Anal. Calcd. for C$_{26}$H$_{22}$O$_8$S.0.4H$_2$O: C, 62.24; H, 4.58; N, 0.00. Found: C, 62.16; $^{-H}$ 4.53; N, 0.10.

EXAMPLE 4

4-[4-(2-Ethyl-benzofuran-3-carbonyl)-2,6-diisopropyl-phenoxysulfonyl]-2-hydroxy-benzoic acid At 5° C., to a stirred suspension containing 2-n-ethyl-3-(4-hydroxy-3,5-diisopropylbenzoyl)benzofuran (0.300 g, 0.856 mmol, RN 52901-28-7) and 0.05M Tris buffer pH 9 (3.41 mL) in THF (1.03 mL) was added dropwise, a solution of 4-chlorosulphonyl-2-hydroxybenzoic acid (0.243 g, 1.03 mmol) in THF (2.05 mL) while maintaining the pH at 10 with the simultaneous addition of 2N NaOH. After the addition was complete, the reaction was stirred for 1.5h. To the reaction was added 4-chlorosulphonyl-2-hydroxybenzoic acid (0.243 g, 1.03 mmol) in THF (2.05 mL) while maintaining the pH at 10 with the simultaneous addition of 2N NaOH. and the reaction was stirred for 1.5h. The reaction was quenched with 2N HCl (40 mL) and extracted with EtOAc. The combined organic extracts were washed with 2N HCl (3×), dried ($MgSO_4$) and concentrated. The crude product was purified by preparative HPLC (C18, eluting with 75% $CH_3CN/H_2O$ containing 0.1% TFA) to give 0.30 g (64%) of the title compound as a white solid, mp 200–201° C.; $^1H$ NMR (DMSO-d6)δ1.05 (d, 12 H), 1.24 (t, 3 H), 2.80 (q, 2 H), 3.09 (septet, 2 H), 7.26 (dt, 1 H), 7.32–7.36 (m, 2 H), 7.45 (d, 1 H), 7.49 (dd, 1 H), 7.62 (s, 2 H), 7.64–7.66 (m, 1 H), 8.06 (d, 1 H).IR (KBr) 3400, 2950, 1680, 1620, 1490 and 1190 $cm^{-1}$. mass spectrum (EI), m/z 550 (M +). Anal. Calcd. for $C_{30}H_{30}O_8S \cdot 0.8H_2O$: C, 63.77; H. 5.64; N, 0.00. Found: C, 63.81; H, 5.55; N, 0.10.

EXAMPLE 5

4-[4-(2-Benzyl-4,5-dimethyl-furan-3-carbonyl)-2,6-diisopropyl-phenoxysulfonyl]-2-hydroxy-benzoic acid Step 1
2-Benzyl-4.5-dimethylfuran At −78° C., to a stirred solution of commercial 2,3-dimethylfuran (50 g, 0.520 mol) in THF (2.6 L) was add dropwise 1.6M n-BuLi/hexanes (325 mL, 0.520 mol). After the addition was complete, the dry ice/acetone bath was removed and the reaction was stirred for 1h. At −78° C., to the reaction was added dropwise commercial benzyl bromide (62 mL, 0.520 mol). After the addition was complete the reaction was stirred at −78° C. for 6h, the dry ice/acetone bath was removed and the reaction was stirred for 7 days. The reaction was concentrated in vacuo and purified on silica gel eluting with hexane to give 75.70 g (78%) of the title compound as a clear oil; $^1H$ NMR (DMSO-d6) δ1.83 (s, 3 H), 2.08 (s, 3 H), 3.83 (s, 2 H), 5.83 (s, 1 H), 7.16–7.30 (m, 5 H). mass spectrum (EI), m/z 186 (M+).

Step 2
(2-Benzyl-4,5-dimethyl-furan-3-yl)-(3,5-diisopropyl4-methoxy-phenyl)-methanone At ambient temperature, to a stirred suspension containing 3,5-diisopropyl-p-anisic acid (1.95 g, 8.23 mmol, RN-1 17439-59-5) and oxalyl chloride (0.8 mL, 9.20 mmol) in $CH_2Cl_2$ (22.5 mL) was added N,N-dimethylformamide (2 drops). After 2h, the reaction was cooled to −78° C. To the reaction was added tin (TV) chloride (1.05 mL) followed by a solution of 2-benzyl4,5-dimethylfuran (1.8 g, 9.68 mmol) in $CH_2Cl_2$ (10.0 mL). After the additions were complete, the reaction was allowed to warm to ambient temperature and stirred for 24 h. The reaction was quenched into crushed ice (100 g), diluted with sat. aq. $KH_2PO_4$ (100 mL) and extracted with ether. The combined ethereal extracts were washed with sat aq. $NaHCO_3$ (2×60 mL), with brine (1×60 ml), dried ($Na_2SO_4$) and concentrated. The crude product was purified on Biotage KP-Sil eluting with 1% EtOAc/pet. ether to give 2.07 g, (62%) of the title compound as an oil; $^1H$ NMR (DMSO-d6)67 1.17 (d, 12 H), 1.81 (s, 3 H), 2.19 (s, 3 H), 3.29 (septet, 2 H), 3.74 (s, 3 H), 3.84 (s, 2 H), 7.01–7.03 (m, 2 H), 7.16–7.25 (m, 3 H), 7.47 (s,2H). mass spectrum (EI), m/z 404 (M+). Anal. Calcd. for $C_{27}H_{32}O_3 \cdot 0.6H_2O$: C, 78.07; H, 8.06; N, 0.00. Found: C, 78.04; H, 7.93; N, −0.02.

Step 3
(2-Benzyl4.5-dimethyl-furan-3-yl)-(3 .5-diisopropyl-4-hydroxy-phenyl)-methanone At −78° C., to a stirred solution of (2-benzyl-4,5-dimethyl-furan-3-yl)-(3,5-diisopropyl-4-methoxy-phenyl)-methanone (2.00 g, 4.94 mmol) in $CH_2Cl_2$ (16.6 mL) was added 1M boron tribromide/$CH_2Cl_2$ (10.4 mL). After the addition was complete, the dry ice/acetone bath was replaced with an ice bath and the reaction was stirred for 1.5 h. The reaction was quenched into crushed ice (18 g), diluted with $H_2O$(20 mL) and extracted with ether. The combined ethereal extracts was washed with brine, dried ($MgSO_4$) and concentrated. The crude product was purified on silica gel eluting with 15% acetone/hexane to give 0.97 g (50%) of the titde compound as a white solid, mp 138° C.; $^1H$ NMR (DMSO-d6) δ1.14 (d, 12 H), 1.80 (s, 3 H), 2.19 (s, 3 H), 3.34 [septet (under $H_2O$ peak), 2 H], 3.84 (s, 2 H), 7.04 (d, 2 H), 7.17–7.25 (m, 3 H) 7.44 (s, 2 H), 9.11 (s, 1 H). IR (KBr) 3400, 2950, 1580, 1320, 1200 $cm^{-1}$. mass spectrum (EI), m/z 390 (M +). Anal. Calcd. for $C_{26}H_{30}O_3 \cdot 0.2H_2O$: C, 79.24; H, 7.77; N, 0.12. Found: C, 79.27; H, 7.85; N, 0.12.

Step 4
4-[4-(2-Benzyl-4,5-dimethyl-furan-3-carbonyl)-2,6-diisolprolpyl-phenoxysulfonul]2-hydroxy-benzoic acid The title compound was prepared according to the procedure in Example 4 using (2-benzyl-4,5-dimethyl-furan-3-yl)-(3,5-diisopropyl-4-hydroxy-phenyl)-methanone (0.300 g, 0.768 mmol) and 4-chlorosulphonyl-2-hydroxybenzoic acid (0.218 g, 0.922 mmol) to give 0.04 g (9%) of the title compound as a tan solid, mp 142–143° C.; $^1H$ NMR (DMSO-d6) δ1.04 (d, 12 H), 1.81 (s, 3 H), 2.19 (s, 3 H), 3.07 (septet, 2 H), 3.81 (s, 2 H), 6.95–6.97 (m, 2 H), 7.14–7.20 (m, 3 H), 7.40–7.46 (m, 2 (s, 2 H), 8.03 (d, 1 H). IR (KBr) 3400, 2950, 1675, 1375, 1180 $cm^{-1}$. mass spectrum (EI), m/z 590 (M+). Anal. Calcd. for $C_{33}H_{34}O_8S \cdot 1.1H_2O$: C, 64.92; H, 5.98; N, 0.00. Found: C, 64.92; H, 5.76; N, −0.03.

EXAMPLE 6

4-[5'-(2-Ethyl-benzofuran-3-carbonyl)-[1,1': 3',1"] terphenyl-2'-yloxysulfonyl-]2-hydroxy-benzoic acid sodium salt Step 1
3,5-Diiodo-4-(2-methoxyethoxymethoxy)benzaldehyde The title compound was prepared according to the procedure in Example 2, step 2 using 3,5-diiodo-4-hydroxybenzaldehyde (10.03 g, 26.83 mmol), 60% NaH/mineral oil (1.395 g, 34.87 mmol) and MEM chloride (4.902 mL, 42.92 mmol) to give 12.81 g, of the title compound. $^1H$ NMR (DMSO-d6) δ3.27 (s, 3 H), 3.54 (t, 2 H), 4.02 (t, 2 H), 5.24 (s, 2 H), 8.34 (s, 2 H), 9.84 (s, 1 H).

Step 2
2'-(2-Methoxyethoxymethoxy)-[1,1';3',1"]terphenyl-5'-carbaldehyde

The tile compound was prepared according to the procedure in Example 2, step 3 using 3,5-diiodo-4-(2-methoxyethoxymethoxy)benzaldehyde (4.029 g, 8.721 mmol), phenylboronic acid (2.339 g, 19.19 mmol), palladium(II) acetate (39.16 mg, 0.174 mmol) in DME:$H_2O$. Purification on Biotage KP-Sil eluting with 15% EtOAc/pet. ether gave 1.803 g, (57%) of the title compound. $^1H$ NMR (DMSO-d6) δ2.78–2.82 (m, 2 H), 2.89–2.92 (m, 2 H), 3.01 (s, 3 H), 4,42 (s, 2 H), 7.40–7.54 (m, 6 H), 7.62∝7.65 (m, 4 H), 7.91 (s, 2 H), 10.06 (s, 1 H).

Step 3
2'-(2-Methoxyethoxymethyl)-[1,1 ';3',1"]terphenyl-5'-carboxylic acid

At ambient temperature, to a stirred mixture of silver (I) oxide (0.570 g, 2.46 mmol) in $H_2O$ (9.8 mL) was added NaOH (0.983 g, 24.6 mmol) and the reaction was heated at 50° C. After 0.5 h, to the reaction was added a solution of 2'-(2-methoxyethoxymethoxy)-[1,1';3',1"]terphenyl-5'-carbaldehyde (1.78 g, 4.92 mmol) in THF (9.8 mL) and the reaction was heated at 90° C. for 1 h. To the reaction was added silver (I) oxide (0.570 g, 2.46 mmol), NaOH (0.983 g, 24.6 mmol) and $H_2O$(10.0 ML). The reaction was heated at 90° C. for 16 h. The reaction was filtered through a celite pad, rinsing with hot $H_2O$(3×). The filtrate was washed with ether (3×), acidified with 2N HCl (pH 2) and extracted with EtOAc. The organic extracts were dried ($MgSO_4$) and concentrated to give 1.73 g (93%) of the title compound. $^1H$ NMR (DMSO-d6) δ2.77–2.80 (m, 2 H), 2.88–2.91 (m, 2 H), 3.01 (s, 3 H), 4.39 (s, 2 H), 7.39–7.52 (m, 6 H), 7.59–7.62 (m, 4 H), 7.89 (s, 2 H), 13.07 (s, 1 H).

Step 4

2'-(2-Methoxyethoxymethyl)-[1,1';3',1"]terphenyl-5'-carboxylic acid methyl ester At 0° C., to a stirred solution of 2'-(2-methoxyethoxymethoxy)-[1,1';3',1"]terphenyl-5'-carboxylic acid (1.72 g, 4.55 mmol) in THF (4.55 mL) was added 1,8-diazabicyclo[5.4.0]undec-7-ene. After 0.5 h, to the reaction was added iodomethane and the reaction was stirred for 16 h, eventually warming to ambient temperature. The reaction was filtered and the filtrate concentrated. The crude product was dissolved in EtOAc, washed sequentially with sat. aq. $NaHCO_3$ (3×), with 1 N HCl (3×), brine (3×), dried ($K2CO_3$) and concentrated. Purification on Biotage KP-Sil eluting with 20% acetone\hexane gave 1.641 g (92%) of the title compound as a yellow oil. $^1H$ NMR (DMSO-d6) δ2.77–2.80 (m, 2 H), 2.88–2.91 (m, 2 H), 3.01 (s, 3 H), 3.87 (s, 3 H), 4.40 (s, 2 H), 7.40–7.53 (m, 6 H), 7.60–7.62 (m, 4 H), 7.90 (s,2 H).

Step 5

2'-Hydroxy-[1,1';3',1"]terphenyl-5'-carboxylic acid methyl ester

At ambient temperature, to a stirred solution of 2'-(2-methoxyethoxymethoxy)-[1,1';3',1"]terphenyl-5'-carboxylic acid methyl ester (1.608 g, 4.098 mmol) in $CH_2Cl_2$ (16.08 mL) was added portionwise trifluoroacetic acid (16.08 mL). After 1 h, the reaction was diluted with ether (100 mL), washed sequentially with $H_2O$ (3×), with sat. aq. $NaHCO_3$ (3×), with brine (3×), dried ($MgSO_4$) and concentrated to give 1.240 g (99%) of the title compound as a white solid. $^1H$ NMR (DMSO-d6) δ3.83 (s, 3 H), 7.39–7.50 (m, 6 H), 7.55–7.57 (m, 4 H), 7.78 (s, 2 H), 9.28 (s, 1 H).

Step 6

2'-Methoxy-[1,1';3',1"]terphenyl-5'-carboxylic acid methyl ester

At ambient temperature, to a stirred mixture containing 2'-hydroxy-[1,1';3',1"]terphenyl-5"-carboxylic acid methyl ester (1.232 g, 4.049 mmol) and $K_2CO_3$ (0.6155 g, 4.454 mmol) in N,N-DMF (10.1 mL) was added iodomethane (0.353 mL, 5.67 mmol). After 18 h, the reaction was diluted with $H_2O$ (100 mL) and the reaction was stirred vigorously. The resulting precipitate was collected, dissolved in $CH_2Cl_2$, dried ($K_2CO_3$) and concentrated to give 1.167 g, (99%) of the tide compound. $^1H$ NMR (DMSO-d6) δ3.16 (s, 3 H), 3.87 (s, 3 H), 7.41–7.53 (m, 6 H), 7.58–7.60 (m, 4H) 7.89 (s, 2 H).

Step 7

2'-Methoxy-[1,1'; 3',1"]terphenyl-5'-carboxylic acid

At ambient temperature, to a stirred solution of 2'-methoxy-[1,1';3',1"]terphenyl-5'-carboxylic acid methyl ester (1.148 g, 3.606 mmol) in THF (36.06 mL) was added 1N KOH (36.06 mL) and the reaction was stirred for 16 h. The reaction was heated at 100° C. for an additional 24 h. The reaction was cooled to ambient temperature, diluted with ether (100 mL) and extracted with 0.1N NaOH. The aqueous extracts were washed with ether (3×), acidified with 6N HCl and extracted with EtOAc. The organic extracts were dried ($MgSO_4$) and concentrated to give 1.043 g (95%) of the tide compound. $^1H$ NMR (DMSO-d6) δ3.15 (s, 3 H), 7.40–7.52 (m, 6 H), 7.58–7.60 (m, 4 H), 7.88 (s, 2 H), 13.04 (s, 1 H).

Step 8

(2-Ethyl-benzofuran-3-yl)-(2'-methoxy-[1,1';3',1"] terphenyl-5'-yl)-methanone

The title compound was prepared according to the procedure in Example 5, step 2 using 2'-methoxy-[1,1';3',1"] terphenyl-5'-carboxylic acid (1.031 g, 3.388 mmol), oxalyl chloride (0.325 mL, 3.727 mmol), commercial 2-ethylbenzofuran (0.4953 g, 3.388 mmol) and tin (IV) chloride (0.436 mL, 3.727 mmol) in $CH_2Cl_2$. Purification on Biotage KP-Sil eluting with 3% EtOAct pet. ether gave 1.070 g, (73%) of the title compound. $^1H$ NMR (DMSO-d6) δ1.24 (t, 3 H), 2.90 (quartet, 2 H), 3.21 (s, 3 H), 7.30–7.67 (m, 14 H), 7.75 (s, 2 H).

Step 9

(2-Ethyl-benzofuran-3-yl)-(2'-hydroxy-[1';3',1"]triphenyl-5'-yl)-methanone

At −78° C., to a stirred solution of (2-ethyl-benzofuran-3-yl)-(2'-methoxy-[1,1';3',1"]terphenyl-5'-yl)-methanone (1.07 g, 2.47 mmol) in $CH_2Cl_2$ (10.1 mL) was added dropwise 1M boron tribromidel $CH_2Cl_2$ (5.2 mL). After the addition was complete, the dry ice/acetone bath was replaced with an ice water bath and the reaction was stirred for 72 h, eventually warming to ambient temperature. The reaction was carefully quenched with crushed ice, diluted with H2O (16 mL) and extracted with ether. The ethereal extracts were dried ($MgSO_4$) and concentrated. Purification on Biotage KP-Sil eluting with 15% acetone/hexane gave 0.86 g, (83%) of the title compound as a white solid, mp 142–143° C. $^1H$ NMR (DMSO-d6)δ1.24 (t, 3 H), 2.90 (quartet, 2 H), 7.28–7.66 (m, 16 H), 9.37 (s, 1 H). IR (KBr) 3200, 2950, 1625, 1560 and 1175 $cm^{-1}$. mass spectrum (EI), m/z 418 (M+). Anal. Calcd. for $C_{29}H_{22}O_3$. 0.35$H_2O$: C, 82.00; H, 5.39; N, 0.00. Found: C, 82.06; H, 5.40; N, 0.07.

Step 10

4-[5'-(2-Ethyl-benzofuran-3-carbonyl)-[1,1';3',1"]triphenyl-2'-yloxysulfonyl]-2-hydroxy-benzoic acid sodium salt The free acid of the title compound was prepared according to the procedure in Example 4 using (2-ethyl-benzofuran-3-yl)-(2'-hydroxy-[1,1';3',1"]terphenyl-5'-yl)-methanone (0.307 g, 0.734 mmol) and 4-chlorosulphonyl-2-hydroxybenzoic acid (0.208 g, 0.880 mmol). Purification on Dynamax C18 (85% $CH_3CN/H_2O$ ) followed by crystallization (EtOAc/hexane) gave 0.204 g, (45%) of the free acid as a white solid.

At ambient temperature, to a stirred solution of the free acid (0.204 g, 0.329 mmol) in MeOH (10 mL) was added 25% wt. sodium methoxidelmethanol (71.1 mg, 0.329 mmol). After 0.5 h, the reaction was concentrated to give 0.210 g (100%) of the title compound as a yellow solid, mp-211–212° C. $^1H$ NMR (DMSO-d6) 5 1.25 (t, 3 H), 2.45 (quartet, 2 H), 6.24–6.26 (m, 2 H), 7.28–7.33 (m, 6 H), 7.35–7.47 (m, 8 H), 7.65–7.67 (m, 1 H), 7.73 (s, 2 H). mass spectrum (−ESI), m/z 617 (M−H). Anal. Calcd. for $C_{36}H_{25}O_8SNa$ .1.3$H_2O$: C, 65.11; H, 4.19; N, 0.00. Found: C, 64.96; H, 4.23; N, 0.10.

EXAMPLE 7

4-[5-(2-Benzyl4,5-dimethyl-furan-3-carbonyl)-3-methyl-biphenyl-2-yloxysulfonyl]-2-hydroxy-benzoic acid sodium salt Step 1

3-Iodo-4-hydroxy-5-methylbenzaldehyde

At 5° C., to a stirred solution containing commercial 4-hydroxy-3-methylbenzaldehyde (4.65 g, 34.1 mmol) and sodium hydroxide (2.73 g, 68.25 mmol) in MeOH (171 mL)

was added iodine (10.8 g, 42.7 mmol). The reaction was stirred for 16 h, eventually warming to ambient temperature. The reaction was quenched with 1N HCl (200 mL) and extracted with ether. The ethereal extracts were washed with 10% $Na_2S_2O_3$ (3x), with brine (3x), dried ($MgSO_4$) and concentrated. Purification on Biotage KP-Sil eluting with 70% $CH_2Cl_2$/pet. ether to give 7.28 g (81%) of the tide compound as a yellow solid. $^1$H NMR (DMSO-d6) δ2.30 (s, 3 H), 7.65 (d, J=1.02 Hz, 1 H), 8.09 (d, J=1.91 Hz, 1 H), 9.74 (s, 1 H), 10.25 (s, 1 H).

Step 2
3-Iodo-4-methoxy-5-methylbenzaldehyde

At 5° C., to a stirred solution of 3-iodo-4-hydroxy-5-methylbenzaldehyde (3.53 g, 13.5 mmol) in THF (67.4 mL) was added 60% sodium hydride/mineral oil (0.701 g, 17.5 mmol). After 0.5 h, to the reaction was added dropwise iodomethane (1.34 mL, 21.6 mmol). After 2 h, the reaction was heated at 60° C. After 3 days, the reaction was cooled to ambient temperature, quenched with $H_2O$ (100 mL) and extracted with ether. The ethereal extracts were washed with 1N NaOH (3x), with brine (3x), dried ($K_2CO_3$) and concentrated. Purification on Biotage KP-Sil eluting with 15% acetone/hexane gave 2.24 g (60%) of the title compound. $^1$H NMR (DMSO-d6) δ2.37 (s, 3 H), 3.77 (s, 3 H), 7.78 (s, 1 H), 8.17 (s, 1 H), 9.86 (s, 1 H).

Step 3
6-Methoxy-5-methyl-biphenyl-3-carbaldehyde

The tide compound was prepared according to the procedure in Example 2, step 3 using 3-iodo4-methoxy-5-methylbenzaldehyde (2.24 g, 8.11 mmol), phenylboronic acid (1.09 g, 8.92 mmol), palladium(II) acetate (36.4 mg, 0.162 mmol) and barium hydroxide octahydrate (3.83 g, 12.2 mmol) in DME:$H_2O$. Purification on Biotage KP-Sil eluting with 15% acetone/hexane gave 1.54 g (84%) of the title compound as a yellow oil. $^1$H NMR (DMSO-d6) δ2.37 (s, 3 H), 3.39 (s, 3 H), 7.42–7.59 (m, 5 H), 7.74–7.79 (m, 2 H), 9.96 (s, 1 H).

Step 4
6-Methoxy-5-methyl-biphenyl-3-carboxylic acid

The tide compound was prepared according to the procedure in Example 6, step 3 using 6-methoxy-5-methyl-biphenyl-3-carbaldehyde (1.53 g, 6.77 mmol), silver (I) oxide (1.56 g, 6.77 mmol) and NaOH (2.71 g, 67.7 mmol) to give 1.46 g (89%) of the title compound as a white solid, mp 165–168° C. $^1$H NMR (DMSO-d6) δ2.34 (s, 3 H), 3.36 (s, 3 H), 7.38–7.55 (m, 5 H), 7.71 (d, 1 H), 7.81 (dd, 1 H). IR (KBr) 3400, 2950, 1700, 1600 and 1410 cm$^{-1}$. mass spectrum (EI), m/z 242 (M+). Anal. Calcd. for $C_{15}H_{14}O_3$ 0.2 $H_2O$: C, 73.27; H, 5.91; N, 0.00. Found: C, 73.21; H, 5.93; N, 0.17.

Step 5
(2-Benzyl-4.5-dimethyl-thiophen-3-yl)-(5-methyl-6-methoxy-biphen-3-yl)-methanone The title compound was prepared according to the procedure in Example 5, step 2 using 6-methoxy-5-methyl-biphenyl-3-carboxylic acid (1.39 g, 5.74 mmol), 2-benzyl-4,5-dimethylfuran (1.15 g, 5.74 mmol), oxalyl chloride (0.550 mL, 6.32 mmol), tin (TV) chloride (0.739 mL, 6.32 mmol) and N,N-DMF (2 drops) in $CH_2Cl_2$. Purification on Biotage KP-Sil eluting with 5% EtOAc/pet. ether gave 1.69 g (71%) of the tide compound as a brown oil. $^1$H NMR (DMSO-d6) δ1.84 (s, 3 H), 2.18 (s, 3 H), 2.29 (s, 3 H), 3.38 (s, 3 H), 3.85 (s, 2 H), 7.04–7.07 (m, 2 H), 7.17–7.26 (m, 3 H), 7.38–7.48 (m, 6 H), 7.58 (d, 1 H).

Step 6
(2-Benzyl-4.5-dimethyl-thiophen-3-yl)-(5-methyl-6-hydroxy-biphen-3-yl)-methanone The title compound was prepared according to the procedure in Example 5, step 3 using (2-benzyl-4,5-dimethyl-thiophen-3-yl)-(5-methyl-6-methoxy-biphen-3-yl)-methanone (1.68 g, 4.09 mmol) and 1M boron tribromide/$CH_2Cl_2$ (8.58 mL). Purification on Biotage KP-Sil eluting with 15% acetone/hexane gave 1.29 g (80%) of the title compound. $^1$H NMR (DMSO-d6) δ1.83 (s, 3 H), 2.17 (s, 3 H), 2.25 (s, 3 H), 3.85 (s, 2 H), 7.07–7.10 (m, 2 H), 7.14–7.26 (m, 3 H), 7.33–7.43 (m, 6 H), 7.54 (d, 1 H), 9.31 (s, 1 H).

Step 7
4-[5-(2-Benzyl4,5-dimethyl-furan-3-carbonyl)-3-methyl-biphenyl-2-yloxysulfon]-2-hydroxy-benzoic acid sodium salt The free acid of the tide compound was prepared according to the procedure in Example 4 using (2-benzyl-4,5-dimethyl-thiophen-3-yl)-(5-methyl-6-hydroxy-biphen-3-yl)-methanone (0.302 g, 0.762 =mol) and 4-chlorosulphonyl-2-hydroxybenzoic acid (0.216 g, 0.991 mmol). Purification on Dynamax C18 (80% $CH_3CN$IH20) gave 0.15 g of the free acid.

The sodium salt was prepared according to the procedure in Example 6, step 10 using the free acid (0.15 g, 0.251 mmol) and 25% wt. sodium methoxide (54 mg, 0.251 mmol) in MeOH (7.6 mL) to give the title compound as a yellow solid, mp 187–190° C. $^1$H NMR (DMSO-d6) δ1.84 (s, 3 H), 2.18 (s, 3 H), 2.23 (s, 3 H), 3.83 (s, 2 H), 6.52 –6.56 (m, 2 H), 7.01–7.04 (m, 2 H), 7.14–7.24 (m, 8 H), 7.38 (d, 1 H), 7.56–7.60 (m, 2 H). IR (KBr) 3400, 2950, 1640, 1590 and 1430 cm$^{-1}$. mass spectrum (–ESI) m/z 595 (M–H). Anal. Calcd. for $C_{34}H_{27}O_8SNa$ .1.6 $H_2O$: C, 63.07; H, 4.70; N, 0.00. Found: C, 63.06; H, 4.60; N, 0.04.

EXAMPLE 8

4-[4-(4,5-Dimethyl-2-naphthalen-2-ylmethyl-furan-3-carbonyl)-2,6-diisopropyl-phenoxysulfonyl]-2-hydroxy-benzoic acid Step 1
2-Naphthalen-2-ylmethyl-4,5-dimethylfuran The title compound was prepared according to the procedure in Example 5, step 1 using 2,3-dimethylfuran, 2-(bromomethyl)naphthalene and 1.6M n-BuLi/hexanes in THF. $^1$H NMR (DMSO-d6) δ1.89 (s, 3 H), 2.15 (s, 3 H), 4.08 (s, 2 H), 5.95 (s, 1 H), 7.40 (d, 1 H), 7.45–7.57 (m, 2 H), 7.77 (s, 1 H), 7.83–7.91 (m, 3 H).

Step 2
(2-Naphthalen-2-ylmethy1–4,5-dimethyl-furan-3-yl)-(3,5-diisopropyl-4-methoxy-phenyl)-methanone The title compound was prepared according to the procedure in Example 5, step 2 using 3,5-diisopropyl-p-anisic acid (0.93 g, 3.95 mmol, RN-117439-59-5), oxalyl chloride (0.377 mL, 4.33 mmol), N,N-dimethylformamide (2 drops), tin (IV) chloride (0.507 mL, 4.33 mmol) and 2-naphthalen-2-ylmethyl4,5-dimethylfuiran (0.93 g, 3.94 mmol) in $CH_2Cl_2$. Purification on Biotage KP-Sil eluting with a 2 & 4% EtOAc/pet. ether step gradient gave 0.357 g (20%) of the title compound. $^1$H NMR (DMSO-d6) δ1.14 (d, 12 H), 1.82 (s, 3 H), 2.20 (s, 3 H), 3.27 (septet, 2 H), 3.74 (s, 3 H), 4.02 (s, 2 H), 7.19 (dd, 1 H), 7.45–7.52 (m, 5 H), 7.76–7.79 (m, 3 H).

Step 3
(2-Naphthalen-2-ylmethyl-4.5-dimethyl-furan-3-yl)-(3,5-diisopropyl-4-hydroxy-phenyl)-methanone The title compound was prepared according to the procedure in Example 5, step 3 using (2-naphthalen-2-ylmethyl-4,5-dimethyl-furan-3-yl)-(3,5-diisopropyl-4-methoxy-phenyl)-methanone (1.04 g, 2.29 mmol) and 1M boron tribroride/$CH_2Cl_2$ (4.81 mL) in $CH_2Cl_2$. Purification on Biotage KP-Sil eluting with 15% acetone/hexane gave 0.542 g (54%) of the title compound. $^1$H NMR (DMSO-d6)

δ 1.12 (d, 12 H), 1.82 (s, 3 H), 2.18 (s, 3 H), 3.31 (septet, 2 H), 4.02 (s, 2 H), 7.22 (dd, 1 H), 7.43–7.50 (m, 4 H), 7.55 (s, 1 H), 7.76–7.86 (m, 3 H), 9.12 (s, 1 H).

Step 4
4-14-(4,5-Dimethyl-2-nalhthalen-2-ylmethyl-furan-3-carbonyl)-2,6-diisopropyl-phenoxysulfonyl]-2-hydroxy-benzoic acid The title compound was prepared according to the procedure in Example 4 using (2-naphthalen-2-ylmethyl-4,5-dimethyl-furan-3-yl)-(3,5-diisopropyl-4-hydroxy-phenyl)-methanone (0.300 g, 0.681 mmol) and 4-chlorosulphonyl-2-hydroxybenzoic acid (0.209 g, 0.885 mmol). Purification on Dynamax C18 (80% $CH_3CN/H_2O$) gave 0.240 g (55%) of the title compound as a yellow solid, mp 130–135° C. $^1H$ NMR (DMSO-d6) δ 1.03 (d, 12 H), 1.83 (s, 3 H), 2.20 (s, 3 H), 3.09 (septet, 2 H), 4.01 (s, 2 H), 7.18 (d, 1 H), 7.43–7.48 (m, 5 H), 7.51 (s, 2 H), 7.77–7.79 (m, 2 H). 7.82–7.86 (m, 1 H), 8.05 (d, 1 H). IR (KBr) 3400, 2950, 1700, 1375 and 1190 $cm^{-1}$. mass spectrum (–ESI) m/z 639 (M–H). Anal. Calcd. for $C_{37}H_{36}O_8S$: C, 69.36; H, 5.66; N, 0.00. Found: C, 69.04; H, 5.77; N, 0.04.

EXAMPLE 9

4-{4-[2-(2-Bromo-benzyl)-4.5-dimethyl-furan-3-carbonyl]-2.6-diisopropyl-phenoxysulfonyl}-2-hydroxy-benzoic acid Step 1
2-(2-Bromo-benzyl)-4.5-dimethyl-furan The title compound was prepared according to the procedure in Example 5, step 1 using commercial 2,3-dimethylfuran (1.00 g, 10.4 mmol), commercial 2-bromobenzylbromide (2.60 g, 10.4 mmol) and 1.6M n-BuLi/hexanes (4.16 mL, 10.4 mmol) in THF. Purification on Biotage KP-Sil eluting with 100% pet. ether gave 1.14 g (41%) of the title compound as a clear oil. $^1H$ NMR (DMSO-d6) δ 1.84 (s, 3 H), 2.11 (s, 3 H), 3.96 (s, 2 H), 5.81 (s, 1 H), 7.19 (dt, 1 H), 7.26–7.37 (m, 2 H), 7.60 (dd, 1 H).

Step 2
[2-(2-Bromo-benzyl)-4.5-dimethyl-furan-3-yl]-(3,5-diisopropyl-4-methoxy-phenyl)-methanone The title compound was prepared according to the procedure in Example 5, step 2 using 3,5-diisopropyl-p-anisic acid (0.983 g, 4.16 mmol, RN-117439-59-5), oxalyl chloride (0.398 mL, 4.56 mmol), N,N-dimethylformamide (2 drops), tin (IV) chloride (0.535 mL, 4.58 mmol) and 2-(2-bromo-benzyl)4,5-dimethyl-furan (1.10 g, 4.16 mmol) in $CH_2Cl_2$. Purification on Biotage KP-Sil eluting with 3% EtOAc/pet. ether gave 0.990 g (49%) of the title compound as a clear oil. $^1H$ NMR (DMSO-d6) δ 1.15 (d, 12 H), 1.84 (s, 3 H), 2.18 (s, 3 H), 3.27 (septet, 2 H), 3.73 (s, 3 H), 3.91 (s, 2 H), 7.12–7.16 (m, 2 H), 7.29 (t, 1 H), 7.44 (s, 2 H), 7.50 (d, 1 H).

Step 3
2-(2-Bromo-benzyl)4,5-dimethyl-furan-3-yl]-(3,5-diisopropyl-4-hydroxy-phenyl)-methanone The title compound was prepared according to the procedure in Example 5, step 3 using [2-(2-bromo-benzyl)-4,5-dimethyl-furan-3-yl]-(3,5-diisopropyl-4-methoxy-phenyl)-methanone (0.973 g, 2.01 mmol) and 1M boron tribromide/$CH_2Cl_2$(4.23 mL) in $CH_2Cl_2$. Purification on Biotage KP-Sil eluting with 15% acetone/hexane gave 0.679 g (72%) of the title compound. $^1H$ NMR (DMSO-d6) 5 1.13 (d, 12 H), 1.82 (s, 3 H), 2.18 (s, 3 H), 3.31 (septet, 2 H), 3.94 (s, 2 H), 7.12–7.17 (m, 2 H), 7.30 (dt, 1 H), 7.42 (s, 2 H), 7.52 (d, 1 H), 9.10 (s, 1 H).

Step 4
4-{4-[2-(2-Bromo-benzyl)-4,5-dimethyl-furan-3-carbonyl]-2.6-diisopropyl-phenylsulfonyl}-2-hydroxy-benzoic acid The title compound was prepared according to the procedure in Example 4 using [2-(2-bromo-benzyl)-4,5-dimethyl-furan-3-yl]-(3,5-diisopropyl-4-hydroxy-phenyl)-methanone (0.300 g, 0.639 mmol) and 4-chlorosulphonyl-2-hydroxybenzoic acid (0.197g, 0.831 mmol). Purification on Dynamax C18 (90% $CH_3CN/H_2O$) gave 0.20 g (47%) of the tide compound as a yellow solid, mp 90–95° C. $^1H$ NMR (DMSO-d6) δ 1.06 (d, 12 H), 1.85 (s, 3 H), 2.19 (s, 3 H), 3.07 (septet, 2 H), 3.91 (s, 2 H), 7.14–7.16 (m, 2 H), 7.29 (dt, 1 H), 7.44 (d, 1 H), 7.47–7.52 (m, 4 H), 8.05 (d, 1 H) (KBr) 3400, 2950, 1690, 1380 and 1190 $cm^{31\ 1}$. mass spectrum (–EST) rnz 667/669 (M–H). Anal. Calcd. for $C_{33}H_{33}BrO_8S$: C, 59.19; H, 4.97; N, 0.00. Found: C, 58.82; H, 5.13; N, 0.13.

Example 10

4-{4-[2-(3-Bromo-benzyl)-4.5-dimethyl-furan-3-carbonyl]-2.6-diisopropylphenoxysulfonyl}-2-hydroxy-benzoic acid Step 1
2-(3-Bromo-benzyl)4,5-dimethyl-furan The title compound was prepared according to the procedure in Example 5, step 1 using commercial 2,3-dimethylfuran (5.00 g, 52.0 mmol), commercial 3-bromobenzylbromide (13.0 g, 52.0 mmol) and 2.5M n-BuLi/hexanes (20.8 mL, 52.0 mmol) in THF. Purification on Biotage KP-Sil eluting with 1% EtOAc/pet. ether gave 12.63 g (85%) of the title compound. $^1H$ NMR (DMSO-d6) δ 1.85 (s, 3 H), 2.10 (s, 3 H), 3.86 (s, 2 H), 5.90 (s, .1 H), 7.21–7.30 (m, 2 H), 7.34–7.47 (m, 2 H).

Step 2
[2-(3-Bromo-benzyl)-4.5-dimethyl-furan-3-yl]-(3.5-diisopropyl-4-methoxy-phenyl)-methanone The title compound was prepared according to the procedure in Example 5, step 2 using 3,5-diisopropyl-p-anisic acid (1.02 g, 4.32 mmol, RN-1 17439-59-5), oxalyl chloride (0.415 mL, 4.75 mmol), N,N-dimethylformamide (2 drops), tin (IV) chloride (0.556 mL, 4.75 mmol) and 2-(3-bromo-benzyl)-4,5-dimethyl-furan (1.15 g, 4.32 mmol) in $CH_2Cl_2$. Purification on Biotage KP-Sil eluting with 3% EtOAc/pet ether gave 1.36 g (65%) of the title compound as a yellow clear oil. $^1H$ NMR (DMSO-d6) δ 1.17 (d, 12 H), 1.80 (s, 3 H), 2.20 (s, 3 H), 3.28 (septet, 2 H), 3.74 (s, 3 H), 3.87 (s,2 H), 7.06 (d, 1 H), 7.19 (d, 1 H), 7.24 (s, 1 H), 7.38 (dd, 1 H), 7.46 (s, 2 H ).

Step 3
[2-(3-Bromo-benzyl)-4.5-dimethyl-furan-3-yl]-(3.5-diisopropyl-4-hydroxy-phenyl)-methanone The title compound was prepared according to the procedure in Example 5, step 3 using [2-(3-bromo-benzyl)-4,5-dimethyl-furan-3-yl]-(3,5-diisopropyl-4-methoxy-phenyl)-methanone (1.34 g, 2.78 mmol) and 1M boron tribromide/$CH_2Cl_2$ (5.84 mL) in $CH_2Cl_2$. Purification on Biotage KP-Sil eluting with 15% acetonelhexane gave 0.995 g (73%) of the title compound. $^1H$ NMR (DMSO-d6) δ1.14 (d, 12 H), 1.80 (s, 3 H), 2.19 (s, 3 H), 3.32 (septet, 2 H), 3.87 (s, 2 H), 7.09 (d, 1 H), 7.22 (t, 1 H), 7.26 (s, 1H), 7.39 (d, 1 H), 7.43 (s, 2 H), 9.13 (s, 1 H). IR (KBr) 3350, 2950, 1580, 1560 and 1325 $cm^{-1}$. mass spectrum (EI) m/z 468 (M+). Anal. Calcd. for $C_{26}H_{29}BrO_3$: C, 66.53; H, 6.23; N, 0.00. Found: C, 66.50; H, 6.22; N, 0.08.

Step 4
4-{4-[2-(3-Bromo-benzyl)-4,5-dimethyl-furan-3-carbonyl]-2.6-diisopropyl-phenoxysulfonyl}-2-hydroxy-benzoic acid The tide compound was prepared according to the procedure in Example 4 using [2-(3-bromo-benzyl)-4,5-dimethyl-furan-3-yl]-(3,5-diisopropyl-4-hydroxy-phenyl)-methanone (0.300 g, 0.639 mmol) and 4-chlorosulphonyl-2-hydroxybenzoic acid (0.197 g, 0.831 mmol). Purification on Dynamax C18 (95% CH₃CN/H₂O) gave 0.23 g (54%) of the title compound as an off white solid, mp 148° C. ¹H NMR (DMSO-d6) δ1.06 (d, 12 H), 1.80 (s, 3 H), 2.21 (s, 3 H), 3.08 (septet, 2 H), 3.87 (s, 2 H), 1 H), 7.21 (t, 1 H), 7.25 (s, 1 H), 7.38 (d, 1 H), 7.44 (s, 1 H), 7.48 (dd, 1 H), 7.51 (s, 2 H), 8.06 (d, 1 H). IR (KBr) 3400, 2950, 1680, 1650 and 1180 cm⁻¹. mass spectrum (−ESI) m/z 667 (M−H). Anal. Calcd. for C₃₃H₃₃BrO₈ S: C, 59.19; H, 4.97; N, 0.00. Found: C, 58.86; H, 4.93; N, 0.07.

EXAMPLE 11

4-{4-[2-(4-Bromo-benzyl)4,5-dimethyl-fuiran-3-carbonyl]-2,6-diisopropyl-phenoxysulfonyl}-2-hydroxy-benzoic acid Step 1
2-(4-Bromo-benzyl)4,5-dimethyl-furan The title compound was prepared according to the procedure in Example 5, step 1 using commercial 2,3-dimethylfuiran (5.00 g, 52.0 mmol), commercial 4-bromobenzylbromide (13.0 g,52.0 mmol) and 2.5M n-BuLi/hexanes (20.8 mL, 52.0 mmol) in THF. Purification on Biotage KP-Sil eluting with 1% EtOAc/pet. ether gave 5.72 g (41%) of the title compound. ¹H NMR (DMSO-d6) δ1.84 (s, 3 H), 2.09 (s, 3 H), 3.83 (s, 2 H), 5.87 (s, 1 H), 7.17 (d, 2 H), 7.49 (d, 2 H).

Step 2
[2(4-Bromo-benzyl)-4,5-dimethyl-furan-3-yl]-(3,5-diisopropyl-4-methoxy-phenyl)-methanone The title compound was prepared according to the procedure in Example 5, step 2 using 3,5-diisopropyl-p-anisic acid (1.03 g, 4.35 mmol, RN-117439-59-5), oxalyl chloride (0.417 mL, 4.79 mmol), N,N-dimethylformarnide (2 drops), tin (TV chloride (0.560 mL, 4.79 mmol) and 2-(4-bromo-benzyl)4,5-dimethyl-fuiran (1.15 g, 4.35 mmol) in CH₂Cl₂. Purification on Biotage KP-Sil eluting with 3% EtOAc/pet. ether gave 1.63 g (77%) of the title compound as a yellow clear oil. ¹H NM (DMSO6) δ1.16 (d, 12 H), 1.80 (s, 3 H), 2.19 (s, 3 H), 3.28 (septet, 2 H), 3.74 (s, 3 H), 3.83(s, 2 H), 6.98 (d, 2 H), 7.41 (dd, 2 H), 7.44 (s, 2 H).

Step 3
[2-(4-Bromo-benzyl)-4,5-dimethyl-furan-3-yl]-(3.5-diisoprolpyl-4-hydroxy-phenyl)-methanone The title compound was prepared according to the procedure in Example 5, step 3 using [2-(4-bromo-benzyl)-4,5-dimethyl-furan-3-yl]-(3,5-diisopropyl-4-methoxy-phenyl)-methanone (1.61 g, 3.32 mmol) and 1M boron tribromide/CH₂Cl₂ (6.97 mL) in CH₂Cl₂. Purification on Biotage KP-Sil eluting with 15% acetone/hexane gave 1.37 g (88%) of the title compound. ¹H NMR (DMSO-d6) δ1.12 (d, 12 H), 1.78 (s, 3 H), 2.17 (s, 3 H), 3.30 (septet, 2 H), 3.81 (s, 2 H), 7.01 (dd, 2 H), 7.40 (s, 2 H), 7.42 (d, 2 H), 9.10 (s, 1 H). IR (KBr) 3400, 2950, 1640, 1580 and 1310 cm⁻¹. mass spectrum (EI) m/z 468 (M+). Anal. Calcd. for C₂₆H₂₉BrO₃: C, 66.53; H, 6.23; N, 0.00. Found: C, 66.57; H, 6.39; N, 0.05.

Step 4
4-{4-[2-(4-Bromo-benzyl)-4.5-dimethyl-furan-3-carbonyl]-2,6-diisopropyl-phenoxysulfonyl}-2-hydroxy-benzoic acid The title compound was prepared according to the procedure in Example 4 using [2-(4-bromo-benzyl)-4,5-dimethyl-furan-3-yl]-(3,5-diisopropyl-4-hydroxy-phenyl)-methanone (1.30 g, 2.77 mmol) and 4-chlorosulphonyl-2-hydroxybenzoic acid (1.00 g, 4.22 mmol). Purification on Dynamax C18 (90% CH₃CN/H₂O) gave 0.98 g (53%) of the title compound as an off white solid, mp 165–168° C. ¹H NMR (DMSO-d6) δ1.05 (d, 12 H), 1.80 (s, 3 H), 2.19 (s, 3 H), 3.06 (septet, 2 H), 3.81 (s, 2 H), 6.92 (d 2 H), 7.39 (dd, 2 H), 7.44 (s, 1 H), 7.45 (s, 2 H), 7.48 (d, 1 H), 8.05 (d, 1 H). IR (KBr) 3400, 2950, 1680, 1375 and 1190 cm⁻¹. mass spectrum (−ESI) m/z 667 (M−H). Anal. Calcd. for C₃₃H₃₃BrO₈S: C, 59.20; H, 4.97; N, 0.00. Found: C, 59.18; H, 5.21; N, 0.08.

EXAMPLE 12

4-{4-[2-(2-Benzyl-benzo[b]thiophen-3-yl)thyl]-phenoxysulfonyl }-2-hydroxy-benzoic acid Step 1
2-Benzyl-benzo[b]thiophene-3-carboxaldehyde Tin chloride (14.0 mL, 119.6 mmol) was added dropwise into a cold (−20 ° C.) solution of 2-benzyl-benzo[b] thiophene (13.4 g, 59.8 mmol) in dichloromethane (150.0 mL). After 1 h, to the reaction was added dropwise dichloromethyl methyl ether (119.6 mmol). The mixture was allowed to gradually come to 0 ° C., and then stirred for 20 hours. The mixture was carefully poured into HCl (2 N) and ice, and extracted with ethyl ether. The ethereal extracts were dried (MgSO₄) and concentrated to give 12.9 g (85%) of the title compound after crystallization from ethyl ether/hexanes, yellow solid mp 86–88 ° C.; mass spectrum m/z 252 (M+). Anal. Calcd. for C₁₆H,l₂O₅: C, 76.16; H, 4.79. Found: C, 75.77; H, 4.85

Step 2
trans-2-Benzyl-3-[2-(4-methoxy-phenyl)-vinyl]-benzo[b]thiophene & cis-2-Benzyl-3-[2-(4-methoxy-phenyl)-vinyl]-benzo[b]thiophene At −78° C., to a stirred suspension of (4-methoxybenzyl) triphenylphosphonium chloride (0.996 g, 2.38 mmol) in THF was added dropwise 1.6M n-BuLi/hexanes (1.36 mL, 2.18 mmol). After 1 h, to the reaction was added dropwise to a solution of 2-benzyl-benzo[b]thiophene-3-carboxaldehyde (5.00 g, 26.8 mmol) in THF that had been previously cooled to −78° C. The reaction was allowed to warm to ambient temperature and stirred for 2 h. The reaction was quenched with H₂O (200 mL), extracted with CH₂Cl₂ and concentrated. Purification on Biotage KP-Sil eluting with a 1% EtOAc/pet ether gave the title compounds as white solids. Analytical data trans isomer; mp 79–81° C. ¹H NMR (DMSO-d6) δ3.66 (s, 3 H), 4.01 (s, 2 H), 6.55 (d, 1 H), 6.71 (d, 2 H), 6.88 (d, 1 H), 7.01 (d, 2 H), 7.13–7.29 (m, 7 H), 7.39–7.42 (m, 1 H), 7.83–7.85 (m, 1 H). IR (KBr) 3100, 2950, 1600, 1510 and 1250 cm⁻¹. mass spectrum (EI) m/z 356 (M+). Anal. Calcd. for C₂₄H₂₀OS .0.2H₂O: C, 80.05; H, 5.71; N, 0.00. Found: C, 80.22; H, 5.86; N, 0.04. Analytical data cis isomer; mp 95–98° C. ¹H NMR (DMSO-d6) δ3.78 (s, 3 H), 4.41 (s, 2 H), 6.95 (d, 2 H), 7.07 (d, 1 H), 7.21–7.24 (m, 1 H), 7.29–7.43 (m, 7 H), 7.61 (d, 2 H), 7.87 (dd, 1 H), 8.06 (d, 1 H). IR (KBr) 3050, 2900, 1700, 1500 and 1250 cm⁻¹. mass spectrum (EI) m/z 356 (M +). Anal. Calcd. for C₂₄H₂₀OS.0.1H₂O: C, 80.46; H, 5.68; N, 0.00. Found: C, 80.40; H, 5.95; N, 0.01.

Step 3
2-Benzyl-3-[2-(4-methoxy-phenyl)-ethyl]-benzo[b]thiophene

At ambient temperature, a mixture of cis and trans-2-benzyl-3-[2-(4-methoxy-phenyl)-viny]-benzo[b]thiophene in EtOAc and 10% palladium on carbon was stirred under H₂ (atmospheric conditions). The reaction was filtered and the filtrate concentrated to give the title compound as a white solid, mp 68–70° C. ¹H NMR; consistent. mass spectrum (EI) m/z 358 (M+). Anal. Calcd. for C₂₄H₂₂OS: C, 80.41; H, 6.19; N, 0.00. Found: C, 80.20; H, 6.18; N, 0.03.

Step 4
4-[2-(2-Benzyl-benzo[b]thiophen-3-yl)-ethyl]-phenol

The title compound was prepared according to the procedure in Example 5, step 3 using 2-benzyl-3-[2-(4- methoxy-phenyl)-ethyl]-benzo[b]thiophene (5.50 g, 15.3 mmol) and 1M boron tribromide/CH$_2$Cl$_2$ (49.1 mL) in CH$_2$Cl$_2$. Purification on silica gel eluting with a 5 & 10% EtOAc/pet. ether step gradient gave the tide compound as an oil. $^1$H NMR; consistent. mass spectrum (EI) m/z 344 (M+).

Step 5
4-{4-[2-(2-Benzy]-benzo[b]thiophen-3-yl)-ethyl]-phenoxysulfonyl}-2-hydroxy-benzoic acid The title compound was prepared according to the procedure in Example 4 using 4-[2-(2-benzyl-benzor[b]thiophen-3-yl)-ethyl]-phenol (0.400 g, 1.16 mmol) and 4-chlorosulphonyl-2-hydroxybenzoic acid (0.550 g, 2.32 mmol). Purification on 2% H$_3$PO$_4$/MeOH treated silica gel, eluting with 20% EtOAc/hexane gave the title compound as an off white solid, mp 57–59° C. $^1$H NMR (DMSO-d6) δ2.74 (t, 2 H), 3.09 (t, 2 H), 4.00 (s, 2 H), 6.97 (d, 2 H), 7.19–7.23 (m, 5 H), 7.27–7.38 (m, 6 H), 7.76 (d 1 H), 7.83 (dd, 1 H), 7.98 (d, 1 H). IR (KBr) 3400, 2950, 1675, 1390 and 1190 cm$^{-1}$ . mass spectrum (–ESI) m/z 543 (M–H).

EXAMPLE 13
4-{4-[2-(4-Bromo-benzyl)4,5-dimethyl-furan-3-carbonyl]-2-cyclopentyl-phenylsulfonyl}-2-hydroxy-benzoic acid Step 1
[2-(4-Bromo-benzyl)-4,5-dimethyl-furan-3-yl]-(3-cyclopentyl-4-methoxy-phenyl)-methanone The title compound was prepared according to the procedure in Example 5, step 2 using 3-cyclopentyl-p-anisic acid (2.04 g, 9.24 mmol, RN-59216-82-9), oxalyl chloride (0.887 mL, 10.2 mmol), N,N-dimethylformamide (2 drops), tin (IV) chloride (1.19 mL, 10.2 mmol) and 2-(4-bromobenzyl)-4,5-dimethyl-furan (2.45 g, 9.24 mmol) in CH2C$_2$. Purification on Biotage KP-Sil eluting with 4% EtOAc/pet. ether gave 3.39 g (78%) of the title compound. $^1$H NMR (DMSO-d6) δ1.38–1.47 (m, 2 H), 1.60–1.73 (m, 4 H), 1.79 (s, 3 H), 1.90–1.94 (m, 2 H), 2.18 (s, 3 H), 3.21 (quintet, 1 H) 3.82 (s, 2 H), 3.88 (s, 3 H), 7.02–7.08 (m, 3 H), 7.44 (d, 2 H), 7.55–7.61 (m , 2 H).

Step 2
[2-(4-Bromo-benzyl)-4,5-dimethyl-furan-3-yl]-(3-cyclopentyl-4-hydroxy-phenyl)-methanone The title compound was prepared according to the procedure in Example 5, step 3 using [2-(4-bromo-benzyl)4,5-dimethyl-faran-3-yl]-(3-cyclopentyl-4-methoxy-phenyl)-methanone (3.38 g, 7.23 mmol) and 1M boron tribromide/CH$_2$Cl$_2$ (15.2 mL) in CH$_2$Cl$_2$. Purification on Biotage KP-Sil eluting with 15% acetone/hexane gave 1.66 g (51%) of the title compound. $^1$H NMR (DMSO-d6) δ1.39–1.48 (m, 2 H), 1.59–1.65 (m, 2 H), 1.68–1.76 (m, 2 H), 1.79 (s, 3 H), 1.88–1.95 (m, 2 H), 2.18 (s, 3 H), 3.18 (quintet, 1 H), 3.81 (s, 2 H), 6.87 (d, 1 H), 7.04 (d, 2 H), 7.43–7.47 (m, 3 H), 7.53 (s, 1 H), 10.35 (s, 1 H). IR (KBr) 3300, 2950, 1650, 1575 and 1280 cm$^{-1}$. mass spectrum (+ESI) m/z 453 (M+H). Anal. Calcd. for C$_{25}$H$_{25}$BrO$_3$: C, 66.23; H, 5.56; N, 0.00. Found: C, 66.12; H, 5.49; N, 0.03.

Step 3
4-{4-[2-(4-Bromo-benzyl)4,5-dimethyl-furan-3-carbonyl]-2-cyclopentyl-phenoxysulfonyl}-2-hydroxy-benzoic acid The title compound was prepared according to the procedure in Example 4 using [2-(4-bromo-benzyl)-4,5-dimethyl-furan-3-yl]-(3-cyclopentyl4-hydroxy-phenyl)-methanone (0.203 g, 0.448 mmol) and 4-chlorosulphonyl-2-hydroxybenzoic acid (0.319 g,1.34 mmol). Purification on Dynamax C18 (85% CH$_3$CNlH$_2$0) gave 0.221 g (49%) of the title compound as a brown solid, mp 188–192° C. $^1$H NMR (DMSO-d6) δ1.26–1.32 (m, 2 H), 1.49–1.57 (m, 2 H), 1.64–1.74 (m, 4 H), 1.77 (s, 3 H), 2.18 (s, 3 H), 2.96 (quintet, 1 H), 3,79 (s, 2 H), 6.96 (d, 2 H), 7.23 (d, 2 H), 7.36 –7.43 (m, 4 H), 7.53–7.56 (m, 2 H), 8.00 (d, 1 H). IR (KBr) 3400, 2950, 1690, 1390 and 1190 cm$^{-1}$. mass spectrum (–ESI) m/z 651 (M–H). Anal. Calcd. for C$_{32}$H2$_9$BrO$_8$S: C, 58.81; H, 4.47; N, 0.00. Found: C, 58.45; H. 4.54; N, 0.07.

EXAMPLE 14
4-{4-[2-(2-Butyl-benzofuran-3-yl)-ethyl]-phenoxysulfonyl}-2-hydroxy-benzoic acid Step 1
2-n-Butylbenzofuran-3-carboxaldehyde At ambient temperature, phosphorous oxychloride (180 mL, 1.94 mol) was carefully added dropwise to N,N-DMF (200 mL). After the addition was complete the reaction was cooled to 10° C. To the reaction was added dropwise commercial 2-butylbenzofuran (240 mL, 1.37 mol) and the reaction was heated to 85° C. for 70 h. The reaction was cooled to ambient temperature and carefully quenched with H$_2$0 (600 mL), adjusted to pH 5 with NaOAc and extracted with ether. The ethereal extracts were washed with H$_2$O, dried (MgSO$_4$) and concentrated. The crude product was purified on silica gel eluting with a 0% & 20% CH$_2$Cl$_2$/hexane step gradient to give 186 g (84%) of the title compound as a yellow oil. $^1$H NMR consistent.

Step 2
cis-2-Butyl-3-[2-(4-methoxu-phenyl)-vinyl]-benzofuran & trans-2-Butyl-3-[2-(4-methoxy-phenyl)-vinyl]-benzofuran The title compound was prepared according to the procedure in Example 12, step 2 using (4-methoxybenzyl)triphenylphosphonium chloride (13.5 g, 32.2 mmol), 1.6M n-BuLi/hexanes (18.5 mL, 29.5 mmol) and 2-n-butylbenzofuran-3-carboxaldehyde (5.00 g, 26.8 mmol). Purification on Biotage KP-Sil eluting with a 10 & 20% toluene/pet. ether step gradient gave the title compounds as oils. Analytical data cis isomer: $^1$H NMR consistent. IR (KBr) 2950, 1600, 1560, 1450 and 1250 cm$^{-1}$. mass spectrum (EI) m/z 306 (M+). Analytical data trans isomer: $^1$H NMR consistent. mass spectrum (EI) m/z 306 (M+).

Step 3
2-Butyl-3-[2-(4-methoxy-phenyl)-ethyl]-benzofuran

At ambient temperature, a solution containing cis-2-butyl-3-[2-(4-methoxy-phenyl)-vinyl]-benzofuran (0.400 g, 1.31 mmol) in EtOAc (5 mL) and 10% palladium on carbon (200 mg) was stirred under H$_2$ (atmospheric conditions). The reaction was fitered and the filtrate concentrated to the title compound as a clear oil. $^1$H NMR (DMSO-d6) δ0.83 (t, 3 H), 1.20 (sextet, 2 H), 1.37 (quintet, 2 H), 2.49–2.52 (m, 2 H, with DMSO), 2.78–2.85 (m, 4 H), 3.68 (s, 3 H), 6.78 (d, 2 H), 7.03 (d, 2 H), 7.17–7.21 (m, 2 H), 7.41–7.43 (m, 1 H), 7.54–7.56 (m, 1 H). IR (KBr) 2950, 1610, 1510, 1450 and 1250 cm$^{-1}$. mass spectrum (EI) m/z 308 (M +). Anal. Calcd. for C$_2$,H$_{24}$O$_2$: C, 81.78; H, 7.84; N, 0.00. Found: C, 81.55; H, 7.57; N, 0.10.

Step 4
4-[2-(2-Butyl-benzofuran-3-yl)-ethyl]-phenol

The title compound was prepared according to the procedure in Example 5, step 3 using 2-butyl-3-[2-(4-methoxyphenyl)-ethyl]-benzofuran (0.300 g, 0.973 mmol) and 1M boron tribromide/CH$_2$Cl$_2$(3.11 mL) in CH$_2$Cl$_2$. Purification on silica gel eluting with 50% EtOAc/pet. ether gave the title compound as a dark oil. $^1$H NMR (DMSO-d6) δ0.84 (t, 3 H), 1.22 (sextet, 2 H), 1.41 (quintet, 2 H), 2.52 (t, 2 H), 2.74 (t, 2 H) 2.81 (t, 2 H), 6.61 (d, 2 H), 6.91 (d, 2 H), 7.15–7.21 (m, 2 H), 7.40–7.43 (m, 1 H), 7.52–7.54 (m, 1 H), 9.10 (s, 1 H). IR (KBr) 3400, 2950, 1610, 1510 and 1450 cm$^{-1}$. mass spectrum (FAB) m/z 295 (M+H).

Step 5
4-{4-[2-(2-Butyl-benzofuran-3-yl)-ethyl]-phenoxysulfony}-2-hydroxy-benzoic acid The title compound was prepared according to the procedure in Example 4 using 4-[2-(2-butyl-benzofuran-3-yl)-ethyl]-phenol (0.410 g, 1.36 mmol) and 4-chlorosulphonyl- 2-hydroxybenzoic acid (0.644 g, 2.72 mmol). Purification on 2% $H_3PO_4$/MeOH treated silica gel, eluting with EtOAc/hexane gave 0.571 g (85%) of the title compound as a light brown solid, mp 93–95° C. $^1H$ NMR consistent. mass spectrum (–ESI) m/z 493 (M–H).

EXAMPLE 15

4-{4-[(2-Butyl-benzofuran-3-ylmethyl)-amino]-phenoxysulfonyl}-2-hydroxy-benzoic acid Step 1
4[(2-Butyl-benzofuran-3-ylmethyl)-amino]-phenol At ambient temperature, to a stirred solution containing 2-n-butylbenzofiran-3-carboxaldehyde (0.888 g, 4.77 mmol) and 4-aminophenol hydrochloride in MeOH (7 mL) was added sodium cyanoborohydride (0.330 g, 5.25 mmol). After 24 h, the reaction was carefully quenched with 3N HCl, diluted with $H_2O$ and extracted with $CH_2Cl_2$. The organic extracts were washed with sat. aq. $NaHCO_3$, dried and concentrated. Purification on silica gel eluting with a 20 & 40% EtOAc/pet. ether step gradient gave the title compound as a pale yellow solid. $^1H$ NMR (CDCl₃) δ8 0.93 (t, 3 H), 1.38 (sextet, 2 H), 1.70 (quintet, 2 H), 2.79 (t, 2 H), 4.27 (s, 1 H), 4.35 (br. s, 1 H), 6.62 (d, 2 H), 6.75 (d, 2 H), 7.18–7.26 (m, 3 H), 7.41 (d, 1 H), 7.54 (d, 1 H).

Step 2
4-{4-[(2-Butyl-benzofuran-3-ylmethyl)-amino]-phenoxysulfonyl}-2-hydroxy-benzoic acid The title compound was prepared according to the procedure in Example 4 using 4-[(2-butyl-benzofuran-3-ylmethyl)-amino]-phenol (0.500 g, 1.69 mmol) and 4-chlorosulphonyl-2-hydroxybenzoic acid (0.401 g, 1.69 mmol). Purification on 2% $H_3PO_4$/MeOH treated silica gel, eluting with 25% EtOAc/hexane gave 0.571 g (85%) of the title compound as a dark yellow solid, mp 75–77° C. $^1H$ NMR (DMSO-d6) δ0.86 (t, 3 H), 1.31 (sextet, 2 H), 1.60 (quintet, 2 H), 2.80 (t, 2 H), 4.23 (s, 2 H), 6.54 (b, 2 H), 6.72 (d, 2 H), 7.14–7.22 (m, 2 H), 7.26–7.30 (m, 2 H), 7.45 (dd, 1 H), 7.58 (dd, 1 H), 7.95 (d, 1 H). IR (KBr) 3400, 2950, 1600, 1510 and 1380 cm$^{-1}$. mass spectrum (–ESI) m/z 494 (M–H).

EXAMPLE 16

4-[4-(2-Butyl-benzofuran-3-carbonyl)-phenylsulfonyl]-2-hydroxy-benzoic acid

The title compound was prepared according to the procedure in Example 4 using commercial 2-n-butyl-3-(4-hydroxybenzoyl)benzofuran (1.00 g, 3.40 mmol) and 4-chlorosulphonyl-2-hydroxybenzoic acid (1.61 g, 6.79 mmol). Purification on :2% $H_3PO_4$/MeOH treated silica gel, eluting with EtOAc/hexane gave 0.185 g (11%) of the title compound as an off white solid, mp 143–145° C. $^1H$ NMR (DMISO-d6) δ0.76 (t, 3 H), 1.12–1.22 (m, 2 H), 1.60 (quintet, 2 H), 2.69 (t, 2 H), 7.21–7.38 (m, 7 H), 7.61 (d, 1 H), 7.76 (d, 2 H), 7.98 (d, 1 H). IR (KBr) 2950, 1690, 1600, 1380 and 1150 cm$^{-1}$. mass spectrum (+ESI) m/z 495 (M+H). Anal. Calcd. for $C_{26}H_{22}O_8S$. $0.2H_2O$: C, 62.24; H, 4.58; N, 0.00. Found: C, 62.38; H, 4.59; N, 0.13.

EXAMPLE 17

4-[4-(2-Benzyl-4,5-dimethyl-furan-3-carbonyl)-2-cyclopentyl-phenoxysulfonyl]-2-hydroxy-benzoic acid Step 1
(2-Benzyl-4,5-dimethyl-furan-3-yl)-(3-cyclopentyl-4-methoxy-phenyl)-methanone The title compound was prepared according to the procedure in Example 5, step 2 using 3-cyclopentyl-p-anisic acid (10.0 g, 45.5 mmol, RN-59216-82-9), oxalyl chloride (4.4 mL, 50.6 mmol), N,N-dimethylformamide (2 drops), tin (IV) chloride (15.8 mL, 49.6 mmol) and 2-benzyl-4,5-dimethyl-furan (10.1 g, 54.3 mmol) in $CH_2Cl_2$ to give 18.8 g (crude) of the title compound. $^1H$ NMR (DMSO-d6) consistent.

Step 2
(2-Benzyl-4.5-dimethyl-furan-3-yl)-(3-cyclopentyl-4-hydroxy-phenyl)-methanone The title compound was prepared according to the procedure in Example 5, step 3 using (2-benzyl-4,5-dimethyl-furan-3-yl)-(3-cyclopentyl4-methoxy-phenyl)-methanone (17.7 g, 45.5 mmol) and 1M boron tribromide/$CH_2Cl_2$ (34.8 mL) in $CH_2Cl_2$. Purification on Biotage KP-Sil eluting with a 2, 5 & 10% EtOAc/pet. ether step gradient gave 6.15 g (36%) of the title compound. $^1H$ NMR (DMSO-d6) δ1.40–1.46 (m, 2 H), 1.59–1.72 (m, 4 H), 1.78 (s, 3 H), 1.90–1.94 (m, 2 H), 2.16 (s, 3 H), 3.18 (quinet, 1 H), 3.81 (s, 2 H), 6.87 (d, 1 H), 7.06 (d, 2 H), 7.16–7.25 (m, 3 H), 7.46 (dd, 1 H), 7.55 (s, 1 H), 10.33 (s, 1 H).

Step 3
4-[4-(2-Benzyl-4.5-dimethyl-furan-3-carbonyl)-2-cyclopentyl-phenoxysulfonyl]-2-hydroxy-benzoic acid The title compound was prepared according to the procedure in Example 4 using (2-benzyl4,5-dimethyl-furan-3-yl)-(3-cyclopentyl-4-hydroxy-phenyl)-methanone (0.509 g, 1.36 mmol) and 4-chlorosulphonyl-2-hydroxybenzoic acid (0.645 g, 2.72 mmol). Purification on 2% $H_3PO_4$/MeOH treated silica gel, eluting with 20% EtOAc/hexane gave 0.430 g (55%) of the title compound a pale yellow solid, mp 80–85° C. $^1H$ NMR (DMSO-d6) δ1.23–1.34 (m, 2 H), 1.45–1.59 (m, 2 H), 1.61–1.74 (m, 4 H), 1.76 (s, 3 H), 2.16 (s, 3 H), 2.95 (quintet, 1 H), 3.78 (s, 2 H), 6.98 (d, 2 H), 7.13–7.25 (m, 4 H), 7.36–7.38 (m, 2 H), 7.44–7.57 (m, 2 H), 7.97 (d, 1 H). IR (KBr) 3400, 2950, 1690, 1580, 1480 and 1190 cm$^{-1}$. mass spectrum (–ESI) m/z 573 (M–H). Anal. Calcd. for $C_{32}H_{30}O_8S$. $0.2H_2O$: C, 66.88; H, 5.26; N, 0.00. Found: C, 66.53; H, 5.40; N, 0.07.

EXAMPLE 18

4-[4-(2-Benzyl-4,5-dimethyl-thiophene-3-carbonyl)-2-cyclopentyl-phenoxysulfonyll-]2-hydroxy-benzoic acid Step 1
2.3-Dimethylthiophene A stirred mixture of commercial 3-methylthiophenecarboxaldehyde (20 g, 0.159 mol), hydrazine hydrate (31 mL) and diethylene glycol (72 mL) was refluxed for 20 min. After cooling below 100° C., potassium hydroxide (22.9 g, 0.408 mol) was slowly added and the reaction mixture was heated at 125–130° C. for 1.5 h. The reaction mixture was cooled to ambient temperature, quenched with $H_2O$ and extracted with ether. The combined ethereal extracts were washed with 5% aqueous HCl, brine, dried ($MgSO_4$) and concentrated. Purification on silica gel eluting with pentane provided the title compound as an oil (15.81 g, 89%): $^1H$ NMR (CDC13) δ6.97 (d, 1H, J=8 Hz), 6.77 (d, 1 H, J=8 Hz), 2.35 (s, 3 H), 2.14 (s, 3 H).

Step 2
2-Benzyl-4.5-dimethylthiophene

The title compound was prepared according to the procedure in Example 5, step 1 using 2,3-dirnethylthiophene (5.00 g, 44.6 mmol), 2.5M BuLi/hexanes (17.9 mL, 44.6 mmol) and benzyl bromide (5.30 mL, 44.6 mmol) in THF (44.6 mL). Purification on Biotage KP-Sil eluting with 1% EtOAc/pet ether gave 6.96 g (77%) of the tide compound as an oil. $^1H$ NMR (DMSO-d6) δ2.01 (s, 3 H), 2.21 (s, 3 H), 3.98 (s, 2 H), 6.58 (s, 1 H), 7.18–7.37 (m, 5 H).

Step 3
(2-Benzyl-4,5-dimethyl-thiophen-3-yl)-(3-cyclopentyl-4-methoxy-phenyl)-methanone The title compound was prepared according to the procedure in Example 5, step 2 using 3-cyclopentyl-p-anisic acid (5.0 g, 22.7 mmol, RN-59216-82-9), oxalyl chloride (2.4 mL, 27.2 mmol), N,N-dimethylformamide (2 drops) tin(IV) chloride (2.9 mL, 25.0 mmol) and 2-benzyl-2,3-dimethylthiophene (5.1 g, 25.0 mmol). Purification on silica gel eluting 5% EtOAc/pet. ether gave 4.8 g (52%) of the title compound as an amber oil. (DMSO-d6) δ7.61–7.54 (m, 2 H), 7.24–7.14 (m, 3 H), 7.08–7.02 (m, 3 H), 3.87 (s, 3 H), 3.84 (s, 2 H), 3.42–3.30 (m, 1 H), 2.26 (s, 3 H), 2.00–1.85 (m, 2 H), 1.81 (s, 3 H), 1.74–1.58 (m, 4 H), 1.48–1.36 (m, 2 H). mass spectrum (EI) m/z 404 (M+). Anal. Calc. for $C_{26}H_{28}O_2S$: C, 77.19, H, 6.98, N, 0.00. Found: C, 76.26, H, 7.24, N, 0.04.

Step 4
(2-Benzyl-4,5-dimethyl-thiophen-3-yl)-(3-cyclopentyl-4-hydrox-phenyl)-methanone The title compound was prepared according to the procedure in Example 5, step 3 using (2-benzyl4,5-dimethyl-thiophen-3-yl)-(3-cyclopentyl-4-methoxy-phenyl)-methanone (3.32 g, 8.20 mmol) and 1M boron tribromide/$CH_2Cl_2$ (1.6 mL) in $CH_2Cl_2$. Purification on Biotage KP-Sil eluting with a 2, 5 & 10% EtOAc/hexane step gradient gave 0.63 g (18%) of the title compound. $^1$H NMR (DMSO-d6) δ consistent.

Step 5
4-(2-Benzyl-4,5-dimethyl-thiophene-3-carbonyl)-2-cyclopentyl-phenoxysulfonyl]-2-hydroxy-benzoic acid The title compound was prepared according to the procedure in Example 4 using (2-benzyl-4,5-dimethyl-thiophen-3-yl)-(3-cyclopentyl-4-hydroxy-phenyl)-methanone (0.505 g, 1.29 mmol) and 4-chlorosulphonyl-2-hydroxybenzoic acid (0.612 g, 2.58 mmol). Purification on 2% $H_3PO_4$/MeOH treated silica gel, eluting with 15% EtOAc/hexane gave 0.432 g (57%) of the title compound a pale yellow solid, mp 70–77° C. $^1$H NMR (DMSO-d6) δ1.29–1.34 (m, 2 H), 1.51–1.57 (m, 2 H), 1.62–1.77 (m,4 H), 1.79 (s, 3 H), 2.25 (s, 3 H), 2.99 (quintet, 1 H), 3.84 (s, 2 H), 6.98 (d, 2 H), 7.12–7.25 (m, 4 H), 7.39 (d, 2 H), 7.52 (dd, 1 H), 7.57 (d, 1 H), 7.99 (d, 1 H), IR (KBr) 3400, 2950, 1690, 1390 and 1190 cm$^{-1}$. mass spectrum (+ESI) m/z 591 (M+H). Anal. Calcd. for $C_{32}H_{30}O_7S_2$.0.5$H_2O$: C, 64.09; H, 5.21; N, 0.00. Found: C, 63.96; H, 5.30; N, 0.04.

EXAMPLE 19

4-[4-(2-Benzyl-4,5-dimethyl-furan-3-carbonyl)-2.6-diethyl-phenoxysulfonyl]-2-hydroxy-benzoic acid Step 1
4-Bromo-2,6-diethylbenzenediazonium tetrafluoroborate At 0° C., to a stirred solution of commercial 4-bromo-2,6-diethylaniline (10.0 g, 43.9 mmol) in absolute ethanol (219 mL) was added 48% aq. tetrafluoroboric acid (17.2 mL), followed by tert-butyl nitrite (5.7 mL, 48.0 mmol). After 0.5 h, the reaction was poured into ice cold ether (877 mL). The resulting precipitate was washed with cold ether and dried to give 9.39 g (66%) of the title compound. $^1$H NMR: consistent.

Step 2
4-Bromo-2.6-diethylanisole

A stirred solution containing 4-bromo-2,6-diethylbenzenediazohium tetrafluoroborate (17.25 g, 52.77 mmol) and freshly ground anhydrous zinc chloride (7.2 g, 52.9 mmol) in methanol (1.06 L) was refluxed for 6 h. The reaction was cooled to ambient temperature, quenched with $H_2O$ (1.2 L), saturated with solid sodium chloride and extracted with hexane. The combined organic extracts were sequentially washed with sat. aq. $NaHCO_3$ (1×100 mL), with $H_2O$ (1×100 mL), with brine (1×100 mL), dried ($Na_2SO_4$) and concentrated to give 12.0 g (94%) of titde compound. $^{-1}$H NMR: consistent. mass spectrum (EI), m/z 242 (M+).

Step 3
3.5-Diethyl-4-methoxybenzoic acid

At −78° C., to a stirred solution of 4-bromo-2,6-diethylanisole (12.0 g, 49.4 mmol) in THF (329 mL) was added dropwise n-butyllithium (27.2 mL, 43.5 mmol). After 3 h, the reaction was poured into crushed dry ice and allowed to warm to ambient temperature. The reaction mixture was diluted with EtOAc, concentrated, suspended in $H_2O$, acidified (pH 1), filtered and the collected solids washed with $H_2O$. The crude product was slurried in hexane (15 mL), collected by filtration and dried to give 6.76 g (66%) of the title compound. $^1$H NMR: consistent. IR (KBr) consistent. mass spectrum (EI), m/z 208 (M+). Anal. Calcd. for $C_{12}H_{16}O_3$: C, 69.21; H, 7.74; N, 0.00. Found: C, 69.28; H, 7.49; N, 0.07.

Step 4
(2-Benzyl-4.5-dimethyl-furan-3-yl)-(3.5-diethyl-4-methoxy-phenyl)-methanone The title compound was prepared according to the procedure in Example 5, step 2, using 3,5-diethyl-4-methoxybenzoic acid (10.66 g, 51.3 mmol), oxalyl chloride (4.90 mL, 56.3 mmol), N,N-DMF (2 drops), tin TV chloride (6.60 mL, 56.3 mmol) and 2-benzyl-4,5-dimethylfuran (11.4 g, 61.3 mmol) to give 22.0 g, of the title compound. $^1$H NMR δ1.13 (t, 6 H), 1.83 (s, 3 H), 2.19 (s, 3 H), 2.61 (q, 4 H), 3.74 (s, 3 H), 3.82 (s, 2 H), 7.05 (d, 2 H), 7.23–7.27 (m, 3 H), 7.42 (s, 2 H). mass spectrum (EI), m/z 376 (M+).

Step 5
(2-Benzyl-4,5-dimethyl-furan-3-yl)-(3.5-diethyl4-hydroxy-phenyl)-methanone The title compound was prepared according to the procedure in Example 5, step 3 using (2-benzyl-4,5-dimethyl-furan-3-yl)-(3,5-diethyl-4-methoxy-phenyl)-methanone (19.3 g, 51.2 mmol) and 1M boron tribromide/$CH_2Cl_2$ (36.8 mL) in $CH_2Cl_2$. Purification on Biotage KP-Sil eluting with a 2 & 5% EtOAc/hexane step gradient gave 7.07 g (37%) of the title compound. $^1$H NMR (DMSO-d6) δ1.08 (t, 6 H), 1.79 (s, 3 H), 2.17 (s, 3 H), 2.57 (q, 4 H), 3.81 (s, 2 H), 7.06 (dd, 2 H), 7.16–7.18 (m, 1 H), 7.22–7.26 (m, 2 H), 7.37 (s, 2 H), 9.10 (s, 1 H). mass spectrum (EI), m/z 362 (M+).

Step 6
4-[4-(2-Benzyl-4,5-dimethyl-furan-3-carbonyl)-2,6-diethyl-phenoxysulfonyl]-2-hydroxy-benzoic acid The title compound was prepared according to the procedure in Example 4 using (2-benzyl-4,5-dimethyl-furan-3-yl)-(3,5-diethyl-4-hydroxy-phenyl)-methanone (0.5 g, 1.38 mmol) and 4-chlorosulphonyl-2-hydroxybenzoic acid (0.65 g, 2.74 mmol). Purification on 2% $H_3PO_4$/MeOH treated silica gel, eluting with 10% EtOAc/hexane gave 0.251 g (32%) of the title compound as an off white solid, mp 143–147° C. $^1$H NMR (DMSO-d6) δ1.01 (t, 6 H), 1.84 (s, 3 H), 2.20 (s, 3 H), 2.51 (q, 4 H, with DMSO peak), 3.81 (s, 2 H), 7.01 (d, 2 H), 7.16–7.20 (m, 1 H), 7.23–7.27 (m, 2 H), 7.45 (s, 2 H), 7.49–7.53 (m, 2 H), 8.06 (d, 1 H). mass spectrum (−ESI), m/z 561 (M−H). Anal. Calcd. for $C_{31}H_{30}O_8S$: C, 66.18; H, 5.37; N, 0.00. Found: C, 65.80; H, 5.50; N, 0.22.

EXAMPLE 20

4-{4-[2-(4-Bromo-benzyl)4.5-dimethyl-thiophene-3-carbonyl]-2-cyclopentylphenoxysulfonyl}-2-hydroxy-benzoic acid Step 1

2-(4-Bromobenzyl)-4,5-dimethylthiophene

The tide compound was prepared according to the procedure in Example 5, step 1 using 2,3-dimethylthiophene (5.10 g, 45.5 mmol), 2.5M BuLi/hexanes (18.2 mL, 45.5 mmol) and 4-bromobenzyl bromide (11.4 g, 45.5 mmol) in THF. Purification on Biotage KP-Sil eluting with 100% pet ether gave 7.74 g (60%) of the title compound. $^1$H NMR: consistent.

Step 2

[2-(4-Bromobenzyl )-4,5-dimethyl-thiophen-3-yl]-(3-cyclopentyl-4-methoxy-phenyl)-methanone The tide compound was prepared according to the procedure in Example 5, step 2 using 3-cyclopentyl-p-anisic acid (3.50 g, 15.9 mmol, RN-59216-82-9), oxalyl chloride (1.52 mL, 17.5 mmol), N,N-dimethylformamide (2 drops) tin(I) chloride (2.04 mL, 17.5 mmol) and 2-(4-bromobenzyl)-4,5-dimethylthiophene (4.46 g, 15.9 mmol). Purification on silica gel eluting 5% EtOAc/pet. ether gave 4.05 g (53%) of the title compound as yellow oil. (DMSO-d6) δ1.43–1.47 (m, 2 H), 1.61–1.75 (m, 4 H), 1.81 (s, 3 H), 1.91–1.99 (m, 2 H), 2.28 (s, 3 H), 3.24 (quintet, 1 H), 3.84 (s,2 H), 3.88 (s, 3 H), 7.02 (d, 2 H), 7.06 (d, 1 H), 7.40 (d, 2 H), 7.52 (dd, 1 H), 7.57 (1 H).

Step 3

[2-(4-Bromobenzyl)-4,5-dimethyl-thiophen-3-yl]-(3-cyclopentyl-4-hydroxy-phenyl)-methanone The title compound was prepared according to the procedure in Example 5, step 3 using [2-(4-bromobenzyl)4,5-dimethyl-thiophen-3-yl]-(3-cyclopentyl-4-methoxy-phenyl)-methanone (4.05 g, 8.39 mmol) and 1M boron tribromide/CH$_2$Cl$_2$(26.0 mL) in CH$_2$Cl$_2$. Purification on Biotage KP-Sil eluting with 15% acetone/hexane gave 2.90 g (74%) of the title compound. (DMSO-d6) δ1.41–1.48 (m, 2 H), 1.59–1.74 (m, 4 H), 1.82 (s, 3 H), 1.89–1.96 (m, 2 H), 2.27 (s, 3 H), 3.20 (quintet, 1 H), 3.84 (s, 2 H), 6.88 (d, 1 H), 7.03 (d, 2 H), 7.39–7.43 (m, 3 H), 7.54 (d, 1 H), 10.47 (s, 1 H).

Step 4

4-{4-[2-(4-Bromo-benzyl)-4,5-dimethyl-thiophene-3-carbonyl]-2-cyclopentyl-phenoxysylfonyl}-2-hydroxy-benzoic acid The title compound was prepared according to the procedure in Example 4 using [2-(4-bromobenzyl)-4,5-dimethyl-thiophen-3-yl]-(3-cyclopentyl-4-hydroxy-phenyl)-methanone (1.01 g, 2.14 mmol) and 4-chlorosulphonyl-2-hydroxybenzoic acid (1.01 g, 4.29 mmol). Purification on 2% H$_3$PO$_4$/MeOH treated silica gel, eluting with a 15 & 25% EtOAc/hexane step gradient followed by crystallization from ether/pet ether gave 0.549 g (38%) of the title compound as a tan solid, mp 165–170° C. $^1$H NMR (DMSO-d6) δ1.22–1.32 (m, 2 H), 1.46–1.58 (m, 2 H), 1.61–1.76 (m, 4 H), 1.78 2.26 (s, 3 H), 2.97 (quintet, 1 H), 3.84 (s, 2 H), 6.94 (d, 2 H), 7.23 (d, 1 H), 7.34–7.40 (m, 2 H), 7.50 (dd, 1 H), 7.53 (d, 1 H), 8.00 (d, 1 H). IR (KBr) 3400, 2950, 1680, 1480, 1390 and 1190 cm$^{-1}$. mass spectrum (–ESI) m/z 667 (M–H). Anal. Calcd. for C$_{32}$H$_{29}$BrO$_7$S$_2$: C, 57.40; H, 4.37; N, 0.00. Found: C, 57.47; H, 4.24; N, 0.08.

EXAMPLE 21

4-{4-[2-(2-Bromo-benzyl)4,5-dimethyl-furan-3-carbonyl]-2-cyclopentyl-phenoxysulfonyl}-2-hydroxy-benzoic acid Step 1

[2-(2-Bromo-benzyl)-4,5-dimethyl-furan-3-yl]-(3-cyclopentyl4-methoxy-phenyl)-methanone The title compound was prepared according to the procedure in Example 5, step 2 using 3-cyclopentyl-p-anisic acid (2.00 g, 9.08 mmol, RN-59216–82–9), oxalyl chloride (0.871 mL, 9.99 mmol), N,N-dimethylformamide (2 drops), tin (IV) chloride (1.17 mL, 4.58 mmol) and 2-(2-bromo-benzyl)-4,5-dimethyl-furan (2.41 g, 9.08 mmol) in CH$_2$Cl$_2$. Purification on Biotage KP-Sil eluting with 4% EtOAc/pet. ether gave 2.82 g (66%) of the title compound as a clear oil. $^1$H NMR (DMSO-d6) δ1.40–1.44 (m, 2 H), 1.57–1.73 (m, 4 H), 1.79 (s, 3 H), 1.87–1.93 (m, 2 H), 2.16 (s, 3 H), 3.21 (quintet, 1 H), 3.86 (s, 3 H),3.93 (s, 2 H), 7.04 (d, 1 H), 7.11–7.18 (m, 2 H), 7.29 (t, 1 H), 7.51 (dd, 1 H), 7.54–7.60 (m, 2 H).

Step 2

[2-(2-Bromo-benzyl)-4,5-dimethyl-furan-3-yl]-(3-cyclopentyl-4-hydroxy-phenyl)-methanone The title compound was prepared according to the procedure in Example 5, step 3 using [2-(2-bromo-benzyl)-4,5-dimethyl-furan-3-yl]-(3-cyclopentyl-4-methoxy-phenyl)-methanone (2.82 g, 6.03 mmol) and 1M boron tribromide/CH$_2$Cl$_2$ (18.7 mL) in CH$_2$Cl$_1$. Purification on Biotage KP-Sil eluting with a 2, 5 & 10% EtOAc/pet. ether step gradient gave 1.36 g (50%) of the title compound. (DMSO-d6) δ1.42–1.44 (m, 2 H), 1.58–1.72 (m, 4 H), 1.79 (s, 3 H), 1.87–1.92 (m, 2 H), 2.16 (s, 3 H), 3.17 (quintet, 1 H), 3.92 (s, 2 H), 6.85 (d, 1 H), 7.12–7.17 (m, 2 H), 7.29 (t, 1 H), 7.45 (dd, 1 H), 7.50–7.52 (m, 2 H), 10.31 (s, 1 H).

Step 3

4-{4-[2-(2-Bromo-benzyl)4.5-dimethyl-furan-3-carbonyl]-2-cyclopentyl-phenoxysulfonyl}-2-hydroxy-benzoic acid The title compound was prepared according to the procedure in Example 4 using [2-(2-bromo-benzyl)-4,5-dimethyl-furan-3-yl]-(3-cyclopenty1–4-hydroxy-phenyl)-methanone (0.516g, 1.14 mmol) and 4-chlorosulphonyl-2-hydroxybenzoic acid (0.540 g, 2.28 mmol). Purification on 2% H$_3$PO$_4$/MeOH treated silica gel, eluting with a 15 & 25% EtOAc/hexane step gradient gave 0.509 g (68%) of the title compound as a brown solid, mp 72–82° C. $^1$H NMR (DMSO-d6) δ1.25–1.34 (m, 2 H), 1.50–1.55 (m, 2 H), 1.62–1.74 (m, 4 H), 1.77 (s, 3 H), 2.15 (s, 3 H), 2.95 (quintet, 1 H), 3.88 (s, 2 H), 7.10–7.15 (m, 2 H), 7.20 (d, 1 H), 7.27 (t, 1 H), 7.35–7.37 (m, 2 H), 7.48–7.58 (m, 3 H), 7.96 (dd, 1 H). IR (KBr) 3400, 2950, 1690, 1390 and 1190 cm$^{-1}$. mass spectrum (–ESI) n/z 651 (M–H). Anal. Calcd. for C$_{32}$H$_{29}$BrO$_8$S. 0.4H$_2$O: C, 58.17; H, 4.55; N, 0.00. Found: C, 58.20; H, 4.55; N, 0.03.

EXAMPLE 22

2-Acetoxy4-[4-(2-benzyl-4,5-dimethyl-furan-3-carbonyl)-2-cyclopentyl-phenoxysulfonyl]-benzoic acid A stirred solution containing 4-[4-(2-benzyl-4,5-dimethyl-furan-3-carbonyl)-2-cyclopentyl-phenoxysulfonyl]-2-hydroxy-benzoic acid (0.235 g, 0.409 mmol), acetic anhydride (3.3 mL) and magnesium iodide (0.113 g, 0.409 mmol) in ether (8 mL) was refluxed for 0.5 h. The reaction was allowed to cool to ambient temperature, quenched with H$_2$O (100 mL), extracted with ether and concentrated. The mixed anhydride/product was dissolved in THF (6 mL), treated with $H_2O$ (6 mL) and refluxed for 0.5 h. The reaction was allowed to cool to ambient temperature, quenched with $H_2O$ (100 mL), extracted with ether and concentrated. Purification on 2% $H_3PO_4$/MeOH treated silica gel, eluting with a 18 & 25% EtOAc/pet ether step gradient followed by crystallization from acetone/hexane gave 0.201 g (80%) of the title compound as an off white solid, mp 55–90° C. $^1$H NMR (DMSO-d6) δ1.23–1.32 (m, 2 H), 1.50–1.53 (m, 2 H), 1.64–1.72 (m, 4 H), 1.76 (s, 3 H), 2.17 (s, 3 H), 2.23 (s, 3 H), 2.92 (quintet, 1 H), 3.79 (s, 2 H), 6.98–7.00 (m, 2 H), 7.15–7.23 (m, 4 H), 7.53 (dd, 1 H), 7.58 (d, 1 H), 7.84 (d, 1 H), 7.88 (dd, 1 H), 8.12 (d, 1 H) 13.7 (br s, 1 H). mass spectrum (–ESI) m/z 615 (M–H). Anal. Calcd. for $C_{34}H_{32}O_9S$ .0.5$H_2O$: C, 65.27; H, 5.32; N, 0.00. Found: C, 65.33; H, 5.30; N, 0.03.

EXAMPLE 23

2-Acetoxy4-[4-(2-benzyl-4,5-dimethyl-thiophene-3-carbonyl)-2-cyclopentyl-phenoxysulfonyl]-benzoic acid The title compound was prepared according to the procedure in Example 22 using 4-[4-(2-benzyl4,5-dimethyl-thiophene-3-carbonyl)-2-cyclopentyl-phenoxysulfonyl]-2-hydroxy-benzoic acid (0.233 g, 0.394 mmol), magnesium iodide (0.110 g, 0.394 mmol) and acetic anhydride (3.3 mL) in ether. Purification on 2% $H_3PO_4$/MeOH treated silica gel, eluting with 18% EtOAc/pet ether followed by a second chromatography on 2% $H_3PO_4$/MeOH treated silica gel, eluting with 5% $CH_3CN/CH_2Cl_2$ gave 0.128 g (51%) of the title compound as a white solid, mp 94–96° C. $^1$H NMR (DMSO-d6) δ1.24–1.33 (m, 2 H), 1.52–1.57 (m, 2 H), 1.61–1.76 (m, 4 H), 1.79 (s, 3 H), 2.23 (s, 3 H), 2.26 (s, 3 H), 2.94 (quintet, 1 H), 3.85 (s, 2 H), 6.99–7.01 (m, 2 H), 7.13 (m, 4 H), 7.52 (dd, 1 H), 7.59 (d, 1 H), 7.84 (d, 1 H), 7.90 (dd, 1 H), 8.14 (d, 1 H), 13.8 (br s, 1 H). mass spectrum (–ESI) m/z 631 (M–H). Anal. Calcd. for $C_{34}H_{32}O_8S_2O$. 0.2$H_2O$: C, 64.17; H, 5.13; N, 0.00. Found: C, 64.06; H, 4.98; N, 0.04.

EXAMPLE 24

2-Acetoxy-4-{4-[2-(4-Bromo-benzyl)-4,5-dimethyl-thiophene-3-carbonyl]-2-cyclopentyl-phenoxysulfonyl}-benzoic acid The title compound was prepared according to the procedure in Example 22 using 4-{4-[2-(4-bromo-benzyl)-4,5-dimethyl-thiophene-3-carbonyl]-2-cyclopentyl-phenoxysulfonyl}-2-hydroxy-benzoic acid (0.211 g, 0.315 mmol), magnesium iodide (0.0876 g, 0.315 mmol) and acetic anhydride (2.5 mL) in ether. Purification on 2% $H_3PO_4$/MeOH treated silica gel, eluting with a 10 & 20% EtOAc/pet ether step gradient followed by crystallization from acetone/hexane gave 0.185 g (57%) of the tide compound as a white solid, mp 113–114° C. $^1$H NMR (DMSO-d6) δ1.27–1.34 (m, 2 H), 1.51–1.58 (m, 2 H), 1.63–1.78 (m, 4 H), 1.80 (s, 3 H), 2.25 (s, 3 H), 2.28 (s,3 H), 2.95 (quintet, 1 H), 3.86 (s, 2 H), 6.97 (d, 2 H), 7.24 (d, 1 H), 7.38 (d, 2 H) 7.52 (dd, 1 H), 7.57 (d, 1 H), 7.86 (d, 1 H), 7.92 (dd, 1 H), 8.16 (d, 1 H) 13.8 (br,s 1 H). mass spectrum (–ESI) m/z 709 (M–H). Anal. Calcd. for $C_{34}H_{31}BrO_8S_2$: C, 57.38; H, 4.39; N, 0.00. Found: C, 56.99; H, 4.38; N, 0.02.

EXAMPLE 25

2-Acetoxy-4-{4-[2-(2-Bromo-benzyl)-4,5-dimethyl-fuiran-3-carbonyl]-2-cyclopentyl-phenoxysulfonyl}-benzoic acid The title compound was prepared according to the procedure in Example 22 using 4-{4-[2-(2-bromo-benzyl)-4,5-dimethyl-furan-3-carbonyl]-2-cyclopentyl-phenoxysulfonyl}-2-hydroxy-benzoic acid (0.318 g, 0.487 mmol), magnesium iodide (0.132 g, 0.475 mmol) and acetic anhydride (3.8 mL) in ether. Purification on 2% $H_3PO_4$/MeOH treated silica gel, eluting with a 30% EtOAc/pet ether gave 0.083 g (25%) of the tide compound as a solid, mp 79° C. $^1$H NMR (DMSO-d6) δ1.27–1.33 (m, 2 H), 1.51–1.54 (m, 2 H), 1.63–1.73 (m, 4 H), 1.79 (s, 3 H), 2.17 (s, 3 H), 2.24 (s, 3 H), 2.93 (quintet, 1 H), 3.91 (s, 2 H), 7.13–7.17 (m, 2 H), 7.21 (d, 1 H), 7.30 (dt, 1 H), 7.51 (dd, 1 H), 7.55 (dd, 1 H), 7.60 (d, 1 H), 7.85 (d, 1 H), 7.90 (dd, 1 H), 8.14 (d, 1 H)13.8 (br s, 1 H). mass spectrum (–ESI) m/z 693/695 (M–H). Anal. Calcd. for $C_{34}H_{31}BrO_9S$: C, 58.71; H, 4.49; N, 0.00. Found: C, 58.04; H, 4.52; N, 0.04.

EXAMPLE 26

2-Acetoxy-4-{4-[2-(2-butyl-benzofuran-3-yl)-ethyl]-phenoxysulfonyl}-benzoic acid At ambient temperature, to a stirred solution containing 4-{4-[2-(2-butyl-benzofuran-3-yl)-ethyl]-phenoxysulfonyl}-2-hydroxy-benzoic acid (0.298 g, 0.602 mmol) and acetic anhydride (1 mL) In EtOAc (2 mL) was added 4-(dimethylamino)pyridine (3.7 mg, 0.0301 mmol). The reaction was refluxed for 72 h. The reaction was cooled to ambient temperature, hydrolyzed with $H_2O$ (5 mL) and stirred for 24 h. The reaction was diluted with EtOAc and the organic phase washed sequentially with $H_2O$ (2×), brine (2×), dried ($MgSO_4$) and concentrated. Purification on 2% $H_3PO_4$/MeOH treated silica gel, eluting with a 10 & 20% EtOAc/pet ether step gradient gave 0.122 g (76%) of the title compound as a yellow solid, mp 54–57° C. $^1$H NMR consistent. IR (KBr) 3400, 2900, 1700, 1380 and 1190 cm$^{-1}$. mass spectrum (–ESI) m/z 535 (M–H).

EXAMPLE 27

1-Methyl-1H-pyrazole-4-sulfonic acid 4-[2-(4-bromo-benzyl)-4,5-dimethyl-thiophene-3-carbonyl]-2-cyclopentyl-phenyl ester Step 1

1-Methyl-1H-pyrazole4-sulfonyl chloride

At 5° C., to stirred chlorosulfonic acid (81.0 mL, 1.22 mol) was cautiously added N-methylpyrazole (25.0 g, 0.304 mol) over a 1 h period. After the addition was complete the reaction was stirred at ambient temperature for 0.5 h, then heated at 110° C. for 16 h. At 5° C., to the reaction was added dropwise thionyl chloride (55.0 mL, 0.754 mol). After the addition was complete the reaction was stirred at ambient temperature for 1 h, then heated to reflux for 2 h. The reaction was cooled to 15° C. and carefully quenched (dropwise) into crushed ice. The title compound was collected by filtration and dried in vacuo to give 37.2 g (68%) of a white solid, mp 51° C. $^1$H NMR (CDCl$_3$) δ4.00 (s, 3 H), 7.95 (s, 1 H), 8.03 (s, 3 H). IR (KBr) 3125, 1700, 1520, 1400 and 1370 cm$^{-1}$. mass spectrum (EI) m/z 180 (M+). Anal. Calcd. for $C_4H_5ClN_2O_2S$: C, 26.60; H, 2.79; N, 15.51. Found: C, 26.25; H, 2.45; N, 15.16.

Step 2

1-Methyl-1H-pyrazole4-sulfonic acid 4-[2-(4-bromo-benzyl)-4,5-dimethyl-thiophene-3-carbonyl]-2-cyclopentyl-phenyl ester At ambient temperature, to a stirred solution of [2-(4-bromobenzyl)-4,5-dimethyl-thiophen-3-yl]-(3-cyclopentyl4-hydroxy-phenyl)-methanone (0.283 g, 0.603 mmol) in N,N-DMF (3.0 mL) was added 60% sodium hydride/mineral oil (24.1 mg, 0.603 mmol). After 0.5 h, to the reaction was added a solution of 1-methyl-1H-pyrazole-4-sulfonyl chloride (0.120 g, 0.664 mmol) in N,N-DNF (1.3 mL). After 3 h, the reaction was quenched with 1N NaOH (40 mL), extracted with $CH_2Cl_2$, dried ($Na_2SO_4$) and concentrated. Purification on Biotage KP-Sil eluting with 20% acetoneihexane gave 0.202 g (55%) of the title compound as a yellow solid, mp 55–60° C. (DMSO-d6) δ1.29–1.34 (m, 2 H), 1.59–1.79 (m, 6 H), 1.81 (s, 3 H), (s, 3 H), 3.08 (quintet, 1 H), 3.87 (s, 2 H), 3.89 (s, 3 H), 6.98 (d, 2 H), 7.32 (d, 1 H), 7.39 (d, 2 H), 7.53–7.57 (m, 2 H), 7.97 (s, 1 H), 8.62 (s, 1 H). IR (KBr) 3450, 2950, 1650, 1490, 1400, 1370 and 1170 $cm^{-1}$. mass spectrum (+ESI) m/z 613/615 (M +H).

EXAMPLE 28

4-[4-(2-Butyl-benzofuran-3-ylmethyl)-phenoxysulfonyl]-2-hydroxy-benzoic acid

Step 1
4-[(2-Butyl-benzofuran-3-yl)-hydroxy-methyl]-phenol

A solution containing commercial 2-n-butyl-3-(4-hydroxybenzoyl)benzofuran (0.500 g, 17.0 mmol) and lithium aluminum hydride (34.0 mmol) in THF (84 mL) was refluxed for 3 h. The reaction was cooled to −10° C., and carefully quenched with 0.1N NaOH and $H_2O$. The aqueous solution was extracted with ether and concentrated. Purification on silica gel gave the title compound as a white solid, mp 94–96° C. (DMSO-d6) δ0.90 (t, 3 H), 1.35 (sextet, 2 H), 1.64 (quintet, 2 H), 2.84 (t, 2 H), 5.6 (d, 1 H), 5.87 (d, 1 H), 6.69 (d, 2 H), 7.07 (t, 1 H), 7.15 (dt, 1 H), 7.22 (d, 2 H), 7.40–7.43 (m, 2 H), 9.24 (s, 1 H). IR (KBr) 3350, 2950, 1610, 1510 and 1450 $cm^{-1}$. mass spectrum (EI) m/z 296 (M+). Anal. Calcd. for $C_{19}H_{20}O_3$ C, 77.00; H, 6.80; N, 0.00. Found: C, 75.63; H, 6.86; N, 0.04.

Step 2
4-(2-Butyl-benzofuran-3-ylmethyl)-phenol

At −10° C., to a stirred solution of 4-[(2-butyl-benzofuran-3-yl)-hydroxy-methyl]-phenol (2.78 g, 9.39 mmol) in $CH_3CN$ was added portionwise triethylsilane (two ×1.50 mL, 18.78 mmol total, @ 0.5 h interval). To the reaction was added $BF_3$ $Et_2O$ (1.19 mL, 9.39 mmol) and the reaction was stirred for 10 min. The reaction was quenched with sat. aq. $K_2CO_3$ and extracted with $CH_2Cl_2$. The organic extracts were washed with brine (3×), dried ($MgSO_4$) and concentrated. Purification on silica gel gave 2.35 g (89%) the title compound as a white solid, mp 67–70° C. (DMSO-d6) δ0.87 (t, 3 H), 1.31 (sextet, 2 H), 1.62 (quintet, 2 H), 2.78 (t, 2 H), 3.84 (s, 2 H), 6.64 (d, 2 H), 7.02 (d, 2 H), 7.09 (dt, 1 H), 7.16 (dt, 1 H), 7.31 (d, 1 H), 7.42 (d, 1 H), 9.16 (s, 1 H). IR (KBr) 3300, 2950, 1610, 1510 and 1450 $cm^{-1}$. mass spectrum (EI) mz 280M +).

Step 3
4-[4-(2-Butyl-benzofuran-3-ylmethy)-phenoxysulfonyl]-2-hydroxy-benzoic acid The tile compound was prepared according to the procedure in Example 4 using 4-(2-butyl-benzofuran-3-ylmethyl)-phenol (0.500 g, 1.78 mmol) and 4-chlorosulphonyl -2-hydroxybenzoic acid (0.844 g, 3.56 mmol). Purification on 2% $H_3PO_4$/MeOH treated silica gel, eluting with EtOAc/hexane gave 0.728 g (86%) of the title compound as an orange solid, mp 135–138° C. $^1$H NMR (DMSO-d6) δ0.84 (t, 3 H), 1.27 (sextet, 2 H), 1.58 (quintet, 2 H), 2.76 (t, 2 H), 3.97 (s, 2 H), 6.96 (d, 2 H) 7.10 (dt, 1 H), 7.17 (dt, 1 H), 7.22–7.31 (m, 5 H), 7.43 (d, 1 H), 7.95 (d, 1 H). IR (KBr) 3300,2950, 1675, 1390 and 1175 $cm^{-1}$. mass spectrum (−ESI) m/z 479 (M−H). Anal. Calcd. for $C_{26}H_{24}O_7S$ $0.2H_2O$: C, 64.50; H, 5.08; N, 0.00. Found: C, 64.50; H, 5.07; N, 0.06.

What is claimed is:

1. A method of treating metabolic disorders mediated by insulin resistance or hyperglycemia in a mammal in need thereof which comprises administering to said mammal, a compound of formula I having the structure

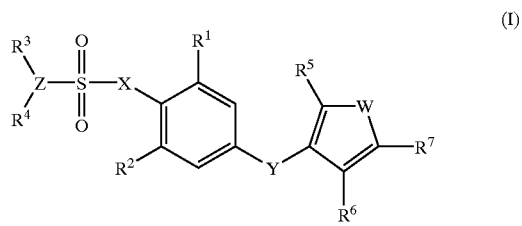

(I)

wherein
$R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl substituted with trifluoromethyl, chloro, methoxy, or trifluoromethoxy;
$R^3$ and $R^4$ are each, independently, hydrogen, carboxyl, hydroxyl, hydoxyalkyl of 1–6 carbon atoms, alkoxy of 1–6 carbon atoms, perfluoroalkoxy of 1–6 carbon atoms, alkanoyloxy of 2–7 carbon atoms, perfluoroalkanoyloxy of 2–7 carbon atoms, arylalkoxy of 7–15 carbon atoms, aryloxy of 6–12 carbon atoms, aroyloxy of 6–12 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, alkylamino of 1–6 carbon atoms, dialkylamino of 1–6 carbon atoms per alkyl group, tetrazolyl mercapto, nitrile, nitro, amino, —$NHSO_2CF_3$, carbamoyl, carboxyaldehyde, halogen, acylamino, 3-hydroxy-cyclobut- 3-ene-4-yl-1,2-dione, pyridyl, isoxazolyl, pyrimidyl or pyrimidyl substituted with mercapto, or tetronic acid;
$R^5$ is hydrogen, alkyl of 1–6 carbon atoms, perfluoroalkyl of 1–6 carbon atoms, naphthalenylmethyl, benzyl or benzyl substituted with halogen,
$R^6$ and $R^7$ are each, independently, hydrogen, alkyl of 1–6 carbon atoms, or perfluoroalkyl of 1–6 carbon atoms, or $R^6$ and $R^7$ may be taken together as a diene unit having the structure —CH=CH—CH=CH—;
W is S or O
X is —$NR^8CH_2$—, —$NR^8$—, or O;
$R^8$ is hydrogen or alkyl;
Y is carbonyl, methylene, ethyl, or —$NHCH_2$—;
Z is phenyl, or naphthyl, or a pharmaceutically acceptable salt thereof.

2. A method of treating or inhibiting type II diabetes in a mammal in need thereof which comprises administering to said mammal, a compound of formula I having the structure

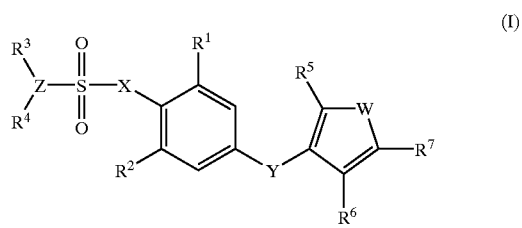

(I)

wherein
$R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl substituted with trifluoromethyl, chloro, methoxy, or trifluoromethoxy;

$R^3$ and $R^4$ are each, independently, hydrogen, carboxyl, hydroxyl, hydoxyalkyl of 1–6 carbon atoms, alkoxy of 1–6 carbon atoms, alkoxy of 1–6 carbon atoms, perfluoroalkoxy of 1–6 carbon atoms, alkanoyloxy of 2–7 carbon atoms, peifluoroalkanoyloxy of 2–7 carbon atoms, arylalkoxy of 7–15 carbon atoms, aryloxy of 6–12 carbon atoms, aroyloxy of 6–12 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, alkylamino of 1–6 carbon atoms, dialkylamino of 1–6 carbon atoms per alkyl group, tetrazolyl, mercapto, nitrile, nitro, amino, —$NHSO_2CF_3$, carbamoyl, carboxyaldehyde, halogen, acylamino, or 3-hydroxy-cyclobut-3-ene-4-yl-1,2-dione, pyridyl, isoxazolyl, pyrimidyl or pyrimidyl substituted with mercapto, or tetronic acid;

$R^5$ is hydrogen, alkyl of 1–6 carbon atoms, perfluoroalkyl of 1–6 carbon atoms, naphthalenylmethyl, benzyl or benzyl substituted with halogen, $R^6$ and $R^7$ are each, independently, hydrogen, alkyl of 1–6 carbon atoms, or perfluoroalkyl of 1–6 carbon atoms, or $R^6$ and $R^7$ may be taken together as a diene unit having the structure —CH=CH—CH=CH—;

W is S or O,

X is —$NR^8CH_2$—, —$NR^8$—, or O;

$R^8$ is hydrogen or alkyl;

Y is carbonyl, methylene, ethyl, or —$NHCH_2$—;

Z is phenyl, naphthyl, pyrazolyl, isoxazolyl, or isothiazolyl; or a pharmaceutically acceptable salt thereof.

3. A method of modulating glucose levels in a mammal in need thereof which comprises administering to said mammal, a compound of formula I having the structure

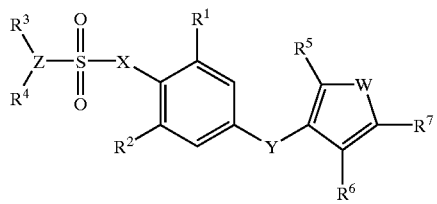

(I)

wherein $R^1$ and $R^2$ are each, independently, hydrogen, alkyl of 1–6 carbon atoms, halogen, perfluoroalkyl of 1–6 carbon atoms, cycloalkyl of 3–8 carbon atoms, thienyl, furyl, phenyl or phenyl substituted with trifluoromethyl, chloro, methoxy, or trifluoromethoxy;

$R^3$ and $R^4$ are each, independently, hydrogen, carboxyl, hydroxyl, hydoxyalkyl of 1–6 carbon atoms, alkoxy of 1–6 carbon atoms, perfluoroalkoxy of 1–6 carbon atoms, alkanoyloxy of 2–7 carbon atoms, perfluoroalkanoyloxy of 2–7 carbon atoms, arylalkoxy of 7–15 carbon atoms, aryloxy of 6–12 carbon atoms, aroyloxy of 6–12 carbon atoms, aryloxycarbonyl of 7–13 carbon atoms, alkoxycarbonyl of 2–7 carbon atoms, perfluoroalkoxycarbonyl of 2–7 carbon atoms, alkyl of 1–6 carbon atoms, perfluoroalkyl of 1–6 carbon atoms, alkylamino of 1–6 carbon atoms, dialkylamino of 1–6 carbon atoms per alkyl group, tetrazolyl, mercapto, nitrile, nitro, amino, —$NHSO_2CF_3$, carbamoyl, carboxyaldehyde, halogen, acylamino, or 3-hydroxy-cyclobut-3-ene-4-yl-1,2-dione, pyridyl, isoxazolyl, pyrimidyl or pyrimidyl substituted with mercapto, or tetronic acid;

$R^5$ is hydrogen, alkyl of 1–6 carbon atoms, perfluoroalkyl of 1–6 carbon atoms, naphthalenylmethyl, benzyl or benzyl substituted with halogen, $R^6$ and $R^7$ are each, independently, hydrogen, alkyl of 1–6 carbon atoms, or perfluoroalkyl of 1–6 carbon atoms, or $R^6$ and $R^7$ may be taken together as a diene unit having the structure —OH=CH—CH=CH—;

W is S or 0,

X is —$NR^8CH_2$—, —$NR^8$—, or O;

$R^8$ is hydrogen or alkyl;

Y is carbonyl, methylene, ethyl, or —$NHCH_2$—;

Z is phenyl, naphthyl, isoxazolyl, or isothiazolyl;

or a pharmaceutically acceptable salt thereof.

* * * * *

UNITED STATES PATENT AND TRADEMARK OFFICE
CERTIFICATE OF CORRECTION

PATENT NO. : 6,683,107 B2
DATED : January 27, 2004
INVENTOR(S) : Paul J. Dollings et al.

It is certified that error appears in the above-identified patent and that said Letters Patent is hereby corrected as shown below:

<u>Title page,</u>
Item [62], Related U.S. Application Priority Data,
"09/564,469" should read -- 09/564,496 --; and
"May 10, 2000" should read -- May 10, 1999 --

Signed and Sealed this

Fourteenth Day of December, 2004

JON W. DUDAS
*Director of the United States Patent and Trademark Office*